(12) United States Patent
Claussen et al.

(10) Patent No.: US 11,536,721 B2
(45) Date of Patent: Dec. 27, 2022

(54) ELECTROCHEMICAL IMMUNOSENSORS

(71) Applicants: IOWA STATE UNIVERSITY RESEARCH FOUNDATION, INC., Ames, IA (US); Brigham Young University, Provo, UT (US)

(72) Inventors: Jonathan Claussen, Ames, IA (US); Suprem Das, Ames, IA (US); Brian D. Iverson, Provo, UT (US)

(73) Assignees: Iowa State University Research Foundation, Inc., Ames, IA (US); Brigham Young University, Provo, UT (US)

( * ) Notice: Subject to any disclaimer, the term of this patent is extended or adjusted under 35 U.S.C. 154(b) by 541 days.

(21) Appl. No.: 16/495,739

(22) PCT Filed: Mar. 26, 2018

(86) PCT No.: PCT/US2018/024375
§ 371 (c)(1),
(2) Date: Sep. 19, 2019

(87) PCT Pub. No.: WO2018/176042
PCT Pub. Date: Sep. 27, 2018

(65) Prior Publication Data
US 2020/0025753 A1 Jan. 23, 2020

Related U.S. Application Data

(60) Provisional application No. 62/476,242, filed on Mar. 24, 2017.

(51) Int. Cl.
G01N 33/543 (2006.01)
G01N 27/327 (2006.01)
G01N 27/30 (2006.01)

(52) U.S. Cl.
CPC ....... *G01N 33/5438* (2013.01); *G01N 27/308* (2013.01); *G01N 27/3275* (2013.01); *G01N 2333/435* (2013.01); *G01N 2469/00* (2013.01)

(58) Field of Classification Search
CPC ........... G01N 27/3278; G01N 27/3275; G01N 27/308; G01N 33/5438; G01N 2333/435; G01N 2469/00
See application file for complete search history.

(56) References Cited

U.S. PATENT DOCUMENTS

| | | | | |
|---|---|---|---|---|
| 2010/0304414 A1* | 12/2010 | Joanis | ............. | G01N 33/56944 435/24 |
| 2012/0070837 A1* | 3/2012 | Huang | ................ | C12Q 1/6886 435/6.12 |

(Continued)

OTHER PUBLICATIONS

Ohno et al. (Biosensors and Bioelectronics, 2013, 422-426) (Year: 2013).*

(Continued)

*Primary Examiner* — Gurpreet Kaur
(74) *Attorney, Agent, or Firm* — Brake Hughes Bellermann LLP

(57) ABSTRACT

In a general aspect, an apparatus can include a first carbon nanotube array that is patterned to define a first electrode having a first plurality of electrode segments. The apparatus can also include a second carbon nanotube array that is patterned to define a second electrode having a second plurality of electrode segments. The second plurality of electrode segments can be interdigitated with the first plurality of electrode segments. The apparatus can further include a biorecognition agent disposed on a surface of the first electrode and disposed on a surface of the second electrode. The first plurality of electrode segments can each have a height-to-width aspect ratio of at least 1 to 1.

22 Claims, 12 Drawing Sheets

(56) References Cited

U.S. PATENT DOCUMENTS

2014/0113127 A1* 4/2014 Tominaga .......... H01B 1/04
977/932
2015/0122669 A1 5/2015 Davis et al.
2016/0022185 A1 1/2016 Agarwal et al.
2016/0146805 A1 5/2016 Iverson et al.

OTHER PUBLICATIONS

Heo et al. (Journal of the Electrochemical Society, 2011, 158, J76-J80). (Year: 2011).*
Hanna et al., Journal of Microelectromechanical system, 2014, 1330-1339. (Year: 2014).*
Kim et al. (Bioconjugate Chem, 2012, 23, 2078-2086). (Year: 2012).*
International Search Report and Written Opinion for International Application No. PCT/US2018/024375, dated Jun. 25, 2018, 12 pages.
Hu et al.: "Development of 3D carbon nanotube interdigitated finger electrodes on polymer substrate for flexible capacitive sensor application" Nanotechnology 24, 444006, Oct. 10, 2013, 14 pages.
Malhotra et al.: "Ultrasensitive Electrochemical Immunosensor for Oral Cancer Biomarker IL-6 using Carbon Nanotube Forest Electrodes and Multilabel Amplification" Anal Chem., 82(8): 3118-3123, Apr. 15, 2010, 13 pages.
Wikipedia, "Carbon nanotube chemistry", Jul. 14, 2016, retrieved on May 21, 2018 from https://en.wikipedia.org/w/index.php?title=Carbon_nanotube_chemistry&oldid=729714747, 8 pages.
Wikipedia, "Oncogene", Oct. 13, 2016, retrieved on May 21, 2018 from https://en.wikipedia.org/w/index.pp?title-Oncogene&oldid=744194924, 5 pages.

* cited by examiner

ELECTROCHEMICAL IMMUNOSENSORS

CROSS REFERENCE TO RELATED APPLICATIONS

This application is a 35 U.S.C. § 371 National Phase Entry Application from PCT Application No. PCT/US2018/024375, filed on Mar. 26, 2018, entitled "ELECTROCHEMICAL IMMUNOSENSORS", and designating the U.S., which claims benefit under 35 U.S.C. § 119 of U.S. Provisional Patent Application No. 62/476,242, filed on Mar. 24, 2017 and entitled "3D Carbon Nanotube, Interdigitated Electrode Architectures for Electrochemical Sensing", the disclosures of which are incorporated by reference herein in their entireties.

TECHNICAL FIELD

This description relates to immunosensors, which can also be referred to as biosensors, for example. In particular, the description relates to three-dimensional electrodes that can be biofunctionalized (e.g., with a biorecognition agent) and used as electrochemical sensors to detect the presence and/or concentration of a target analyte (e.g., in a solution or biological sample).

BACKGROUND

Immunosensing, which can also be referred to as biosensing, can be helpful in the detection and prevention of healthcare risks, such as to detect the presence of cancers, bacterial infections and/or other biological conditions. Current approaches for biosensing are, however, complicated, time consuming, lack precision, and/or are expensive (e.g., requiring laboratory testing). In some instances, such as in the detection of oral cancers, for example, immunosensing or biosensing may not be the primary diagnostic approach used to detect such conditions. As a result, current approaches can impede detection and/or prevention of emerging healthcare threats.

SUMMARY

In a general aspect, an apparatus can include a first carbon nanotube array that is patterned to define a first electrode having a first plurality of electrode segments. The apparatus can also include a second carbon nanotube array that is patterned to define a second electrode having a second plurality of electrode segments. The second plurality of electrode segments can be interdigitated with the first plurality of electrode segments. The apparatus can further include a biorecognition agent disposed on a surface of the first electrode and disposed on a surface of the second electrode. The first plurality of electrode segments can each have a height-to-width aspect ratio of at least 1 to 1.

In another general aspect, an apparatus can include a patterned carbon nanotube array having a height of greater than or equal to 0.5 microns (µm). The apparatus can also include amorphous carbon infiltrated in a surface of the patterned carbon nanotube array and a biorecognition agent disposed on the surface of the carbon nanotube array.

In another general aspect, a method can include forming a first carbon nanotube array including patterning the first carbon nanotube array to define a first electrode having a first plurality of electrode segments. The method can further include forming a second carbon nanotube array including patterning the second carbon nanotube array to define a second electrode having a second plurality of electrode segments. The second plurality of electrode segments can be interdigitated with the first plurality of electrode segments. The method can also include immobilizing a biorecognition agent on a surface of the first electrode and on a surface of the second electrode. The first plurality of electrode segments can each have a height-to-width aspect ratio of at least 1 to 1.

BRIEF DESCRIPTION OF THE DRAWINGS

Like reference symbols in the various drawings indicate like and/or similar elements. The drawings are for purposes of illustration and may not necessarily be to scale. Also, in some views, one or more features of an implementation may be obscured or omitted.

DETAILED DESCRIPTION

Figure 2:
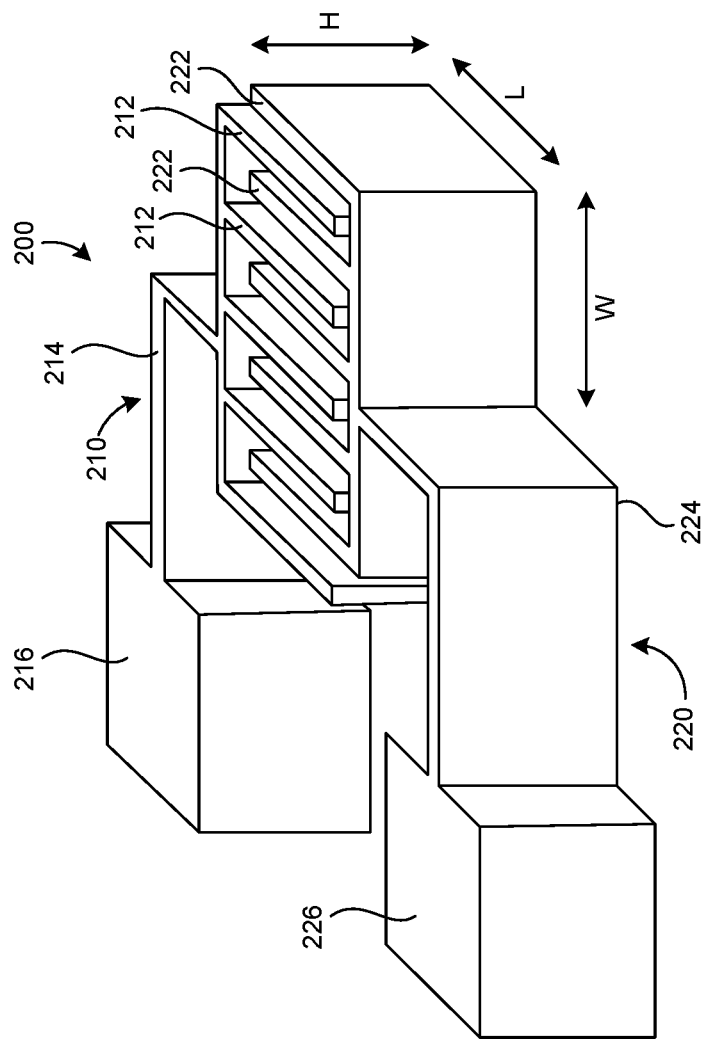
FIG. 2 is a diagram illustrating a sensor (e.g., an immunosensor) including interdigitated electrodes (IDEs) patterned from carbon nanotube forests, such as the ribs of FIG. 1.

In the following description, implementations of electrochemical sensors (biosensors, immunosensors, etc.) and methods for producing such biosensors are described. Also in the following description, evaluation and characterization of such electrochemical sensors for example implementations, including examples of collected empirical data is discussed. While implementations in the following description are generally discussed in the context of electrochemical detection of oral cancer, other uses of such electrochemical sensors are possible, some examples of which are also discussed below.

Oral cancers (OCs) are the thirteenth most common cancers in the world, with approximately 300,000 new cases and 145,000 deaths occurring annually. Despite such cancers affecting one of the most accessible anatomical sites of the human body, early diagnosis of OC, using current approaches can be challenging, and approximately 70% of oral malignancies are diagnosed in advanced stages. As a result, the prognosis of OC patients is generally poor, with the overall 5-year survival rate for OCs being less than 40%.

In an effort to improve OC patient prognosis, a wide variety of OC screening techniques have been developed including visual screening, toluidine blue (TB) staining, auto-fluorescence spectroscopy, exfoliative cytology, and biopsy/histopathology. However, these techniques suffer from drawbacks such as low sensitivity, lack of specificity for malignant tissue, and are also time-consuming, complex, expensive, and/or labor intensive. interleave Electrochemical-based biosensors including three-dimensional (3D) interdigitated (interleaved, interwoven, interspersed, etc.) electrodes (IDEs), such as two electrodes with alternating segments, alternating fingers, etc., such as those described herein. Such biosensor IDEs can be monitored (e.g., measured after exposure to a biological sample) with electrochemical impedance spectroscopy (EIS), can provide significant improvements for point-of-care cancer diagnostics, such as for the detection of oral cancers. IDEs can include alternating, finger-like electrodes or electrode segments that are electrically connected with a width and pitch typically in the range of 5-25 μm. Such 3D IDEs can operate well as electrochemical transducers as they exhibit low ohmic drops, have large collection efficiencies, high signal-to-noise ratios, and fast response times.

EIS can be employed as the sensing modality for IDE-based immunosensors due to its ability to detect small variations in resistance/capacitance, which, using the 3D IDE sensors described herein, provides the ability for label-free, real-time, and in situ detection of various analytes, including oral cancer markers, or other biological markers. Such 3D electrochemical IDE sensors, as discussed herein, have shown the ability to accurately detect cancer linked protein concentrations with low detection limits and wide sensing ranges, as described below.

Using implementations of 3D IDE electrochemical sensors described herein can, using EIS, detect a target analyte without the need for secondary labeling, as is used in current electrochemical immunosensors (biosensors, etc.). For instance, current electrochemical immunosensors can require the use of a secondary Ab label conjugated with either a conductive nanoparticle or enzyme-nanoparticle bioconjugate. Such labeling techniques are utilized to amplify heterogeneous charge transport at the sensor-liquid interface (e.g., in a biological sample), because of the relatively insulating qualities of the biorecognition agents themselves and/or the surface functionalization motifs. Consequently, such labeling requirements increase the complexity of the biosensing protocol and diminish the likelihood of point-of-care (POC) testing, which drawbacks can be overcome using implementations of 3D IDE electrochemical sensors described herein.

As noted above, implementations of EIS 3D IDE immunosensors for detecting a biomarker related to oral cancer (e.g., an oncoprotein CIP2A), as well as to malignancies such as breast cancer and multiple myeloma, are described herein, though such immunosensors can be utilized to detect any number of biomarkers. By way of background, the oncoprotein CIP2A promotes malignant cell growth and tumor progression and is generally overexpressed in most human cancers including lung, breast and gastric cancers. CIP2A expression is, however, even more pronounced in oral cancers, as compared to lung and gastric cancers, with 85% of tongue cancer specimens and 90% of esophageal squamous cell carcinoma specimens scoring moderately or strongly positive for CIP2A expression. Further, CIP2A is abundantly expressed in oral squamous cell carcinoma lines, as well as dysplastic and malignant human oral epithelial tissues. Accordingly, CIP2A biosensors implemented using the 3D IDE sensor implementations disclosed herein can be of significant value towards the development of an oral cancer screening test.

Briefly, the immunosensor implementations disclosed herein are implemented using 3D, high-aspect-ratio carbon nanotube arrays, which can be vertically aligned carbon nanotube arrays (VANTAs) arranged in an IDE footprint. While the implementations described herein are generally discussed in the context of VANTAs, in some implementations, other arrangements of carbon nanotube arrays are possible.

The immunosensors described herein can enable rapid, label-free CIP2A monitoring. For instance, the high surface area of the VANTA IDEs and material properties of carbon nanotubes (CNTs) (e.g., high electrical conductivity, electrochemical reactivity, and biocompatibility) can provide higher biosensor sensitivity than a comparable enzyme-linked immunosorbent assay (ELISA) test kit.

Furthermore, the 3D IDE sensor implementations described herein can be produced using facile lithographic patterning to create (pattern) a seed catalyst metal for formation of CNTs with a micro IDE pattern. Such patterning can be accomplished with significantly less cleanroom processing than other immunosensors, such as field effect transistors (FETs). For instance, production of such FET sensors can require nano/microwire gate development, gate oxide growth, deposition of active source/drain regions, reference electrode deposition, and passivation layer formation. Additionally, cracks, or other defects in the passivation layer of such FET sensors can significantly alter biosensor outputs, leading to false positive/negative signals.

As an additional advantage, the use of VANTA IDE sensors in conjunction with an electrochemical (e.g., EIS) sensing modality can also eliminate the need for target analyte labeling with fluorophores or Førster resonance energy transfer (FRET) dye pairs, which are difficult to characterize and highly variable with in-field biological and/or turbid samples. The use of VANTA IDE sensors in conjunction with EIS sensing can also eliminate the need for sensor pre-enrichment operations that can require upwards of 24-48 hours before biosensor signal acquisition, as is the case with many current lateral flow assayed immunosensors. Furthermore, electrochemical sensing using the 3D VANTA IDE sensors described herein can yield a qualitative signal that can indicate a specific target analyte concentration, as opposed to current colorimetric biosensors that report only qualitative results (e.g., positive or negative). Hence, the biosensor implementations disclosed herein may be highly conducive to in-field point-of-care (POC) diagnostics and detection.

Briefly, the 3D sensors described herein can include VANTAs grown via chemical vapor deposition in an IDE footprint with a height-to-width aspect ratio of the IDE segments of approximately 1:1 (e.g., 25 μm:25 μm). Such VANTA-IDEs can be functionalized (biofunctionalized) with an antibody (Ab) specific to the human cancerous inhibitor PP2A (CIP2A), where CIP2A is a salivary oncoprotein that is associated with, as noted above, a variety of malignancies such as oral, breast, and multiple myeloma cancers. The resultant 3D VANTA IDE immunosensor, as described herein, can be capable of detecting CIP2A label-free across a wide linear sensing range, e.g., 1-100 picograms per milliliter (pg/mL), with a lower concentration detection limit of 0.24 pg/mL within a saliva supernatant (e.g., a turbid sample). This detection range (and detection limit) is more sensitive than existing CIP2A ELISA test kits. Accordingly, the 3D VANTA IDE sensor implementations described herein can facilitate rapid cancer screening tests at a POC, such as for early-stage diagnosis of oral cancers at a dentist's office, using a patient's saliva as the biological sample.

Figure 1:
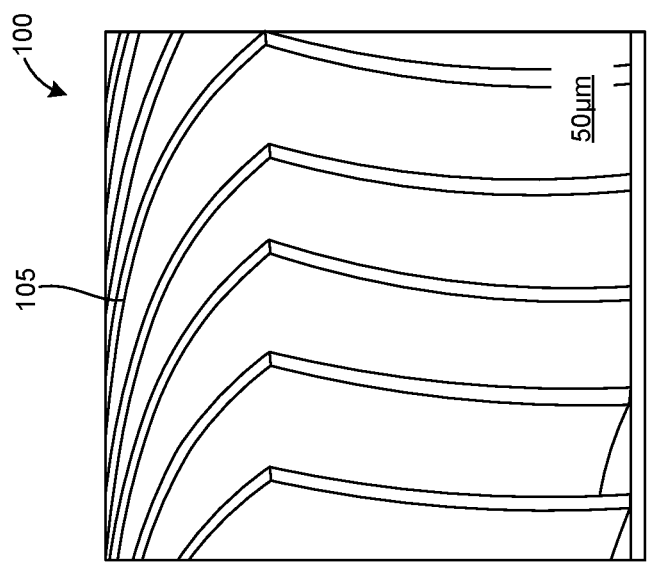
FIG. 1 is a diagram illustrating rib structures that are formed by patterning forests (arrays) of carbon nanotubes, such as vertically aligned carbon nanotubes (VANTAs).

FIG. 1 is a diagram illustrating a patterned CNT forest 100 that defines (forms, etc.) rib structures 105. For instance, the rib structures 105 can be formed by patterning forests (arrays) of vertically aligned carbon nanotubes, or VANTAs. Such rib structures 105 (or similar structures) can be included in 3D VANTA IDE sensors (immunosensor, biosensors, and so forth), such as those described herein.

In some implementations, the rib structures 105 can include patterned CNT forests that have been reinforced with amorphous carbon. Use of the rib structures 105 (or similar structures) in 3D VANATA IDEs for electrochemical sensing can increase capacitance (e.g., as compared with planar sensors) by several orders of magnitude due, at least in part to the high height-to width aspect ratios. Further, such 3D VANTA IDE sensors can provide porous electrodes (IDEs) that have high surface area to volume ratios, and can offer convenient sites for molecular immobilization or functionalization with biorecognition agents. Further, such carbon-coated (e.g., amorphous carbon-coated) CNT structures are highly electrocatalytic and demonstrate excellent electron transport within a corresponding electrochemical structure.

FIG. 2 is a diagram illustrating a sensor 200 (e.g., an immunosensor, biosensor, etc.) including 3D IDEs patterned from VANTAs, such as the rib structures 105 of FIG. 1. As shown in FIG. 2, the sensor 200 can include a first electrode 210 and a second electrode 220. The first electrode 210 and the second electrode 220 can include patterned VANTAs that can be formed using the process described below with respect to FIGS. 3A-3E. The first electrode 210 can include a plurality of interconnected electrode segments 212 (fingers, etc.), and a connecting structure 214 that couples the interconnected electrode segments 212 with contact pad 216. The contact pad 216 can be used for performing EIS measurements on the sensor 200. Similarly, the second electrode 220 can include a plurality of interconnected electrode segments 222, and a connecting structure 224 that couples the interconnected electrode segments 222 with contact pad 226. The contact pad 226 can be used, in conjunction with the contact pad 216, for performing EIS measurements on the sensor 200. As shown in FIG. 2, the electrode segments 222 can be interdigitated (interleaved, interwoven, interspersed, etc.) with the electrode segments 212. The sensor 200 (e.g., the electrodes 210 and 220) can have a biorecognition agent (e.g., PP2A) disposed (immobilized, etc.) on its surface.

In some implementations, the electrode segments 212 and/or the electrode segments 222 can have a height-to-width aspect ratio of at least 1 to 1, where height is measured along the axis H in FIG. 2 and width is measured along the axis W in FIG. 2. Further, in some implementations, the electrode segments 212 and/or the electrode segments 222 can have a length (along the axis L) of approximately 2 millimeters (mm). In some implementations, other dimensions of the sensor 200 are possible and can depend on the specific sensor application (e.g., the target analyte).

In some implementations, the electrode segments 212 and/or the electrode segments 222 can have a width (along the axis W) of approximately 1-100 microns ($\mu m$) and a height (along the axis H) equal to or greater than 0.5 $\mu m$, greater than or equal to 1 $\mu m$, greater than or equal to 10 $\mu m$, greater than or equal to 100 $\mu m$, greater than or equal to 500 $\mu m$, etc. Further, in some implementations, a spacing (along the axis W) between an electrode segment 212 of the first electrode 210 and an adjacent electrode segment 222 of the second electrode 200 can be in a range of 1-25 $\mu m$.

In some implementations, the biorecognition agent of the sensor 200 can include one of an antibody, an aptamer (e.g., DNA) or an enzyme. For instance, as noted above, the biorecognition agent can include an antibody specific to detection of an oncoprotein, such as the PP2A cancerous inhibitor for detecting the CIP2A oncoprotein, or could include other biorecognition agents to detect other corresponding target analytes.

The following discussion of FIGS. 3A-11B describes design, fabrication, characterization and use of 3D VANTA IDE sensor implementations for immunosensing to detect the CIP2A oncoprotein oral cancer biomarker. This discussion also describes empirical data that was collected and statistical modeling associated the described implementations. This discussion is provided for purposes of illustration and is given by way of example. In some implementations, the details discussed above can be included in the implementations discussed with respect to FIGS. 3A-11B. Likewise, the details of the implementations discussed with respect to FIGS. 3A-11B can be included in other electrochemical sensor implementations, such as those described herein.

FIGS. 3A-3E are diagrams illustrating a process of producing an immunosensor (a 3D VANTA IDE sensor) 300 (e.g., which can also be used to implement the immunosensor 200 of FIG. 2), and detection of a corresponding antigen, e.g., the CIP2A oncoprotein. In the following discussion, each operation of FIGS. 3A-3E is first briefly described, followed by a more detailed explanation of an example implementation of the process of FIGS. 3A-3E.

Figure 3C:
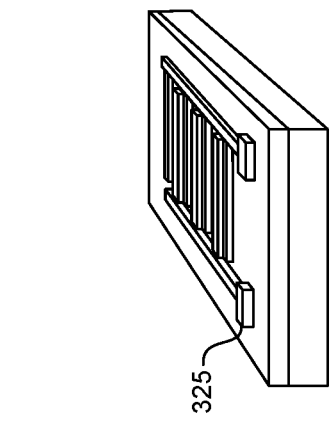
FIGS. 3A-3E are diagrams illustrating a process of producing an immunosensor, such as the immunosensor of FIG. 2 and detection of a corresponding analyte.
Figure 3E:
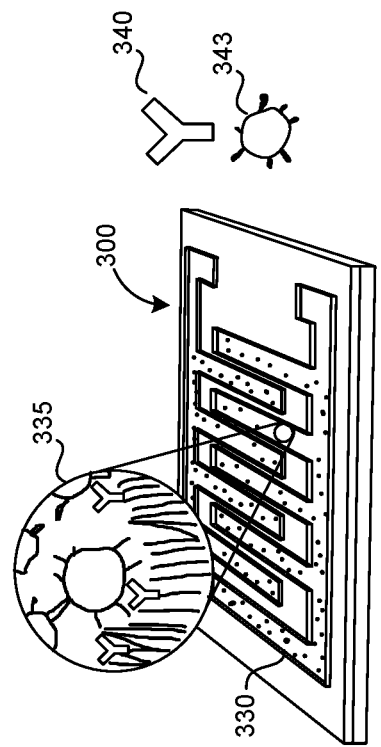
Figure 3B:
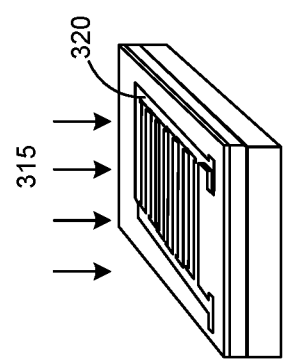
Figure 3A:
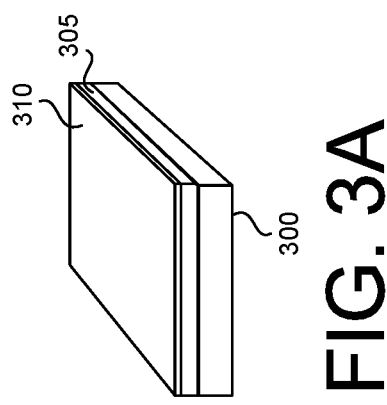
Figure 3D:
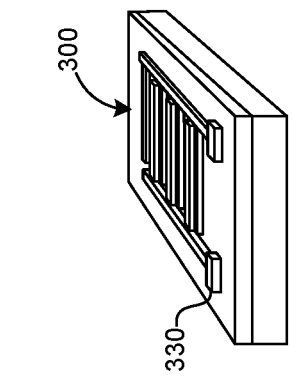

As shown in FIG. 3A, an $Al_2O_3$ buffer layer 305, which can be approximately 50 nanometers (nm), can be formed on a $Si/SiO_2$ wafer 300 using physical vapor deposition and a spin coated photoresist layer 310 can be formed on the buffer layer 305. The buffer layer 305 can prevent migration of a CNT catalyst in to the substrate 300. As shown in FIG. 3B, ultraviolet (UV) lithographic patterning of the IDE footprint 320 in the photoresist 310, using UV light 315, can be followed, as shown in FIG. 3C, by PVD of a CNT catalyst layer 325, which can be an approximately 7 nm thick iron (Fe) layer that is defined in the IDE pattern using photoresist lift-off process. As shown in FIG. 3D, VANTAs 330 can be grown from the catalyst layer 325, which can be followed by in situ amorphous carbon infiltration. In the inset 335 in FIG. 3E, a schematic diagram is shown illustrating an anti-CIP2A antibody (e.g., PP2A) 340 bound to the VANTA IDE sensor 300, with detected CIP2A oncoprotein 343 (which can be referred to as the antigen in this example).

With further reference to the process illustrated by FIGS. 3A-3E, in some implementations, a high-aspect-ratio VANTA IDE sensor 300 (e.g., including a patterned forest of multi-walled CNTs grown with average diameter of 20-30 nm and height of 50-80 $\mu m$) can be synthesized using a chemical vapor deposition (CVD) process. Referring again to FIG. 3A, a silicon wafer 300 with a 300 nm thick, thermally grown oxide was used as a base substrate for fabrication of the sensor 300. As also shown in FIG. 3A, an electron beam (e-beam) was used to deposit an $Al_2O_3$ buffer layer 305 of 50 nm thickness onto the wafer 300 and a photoresist coating layer 310 was then spun onto the buffer layer 305.

As shown in FIG. 3B, the IDE pattern 320 was defined by photolithography, and resist development. As shown in FIG. 3C, a 7 nm iron (CNT catalyst) layer was thermally evaporated onto the wafer, followed by photoresist lift off using N-Methyl-2-pyrrolidone for 10 minutes, leaving the IDE-patterned iron catalyst 325 ready for CNT growth. As shown in FIG. 3D, a tube furnace was used for CNT growth using a controlled flow of hydrogen (311 sccm) and ethylene (338 sccm) at 750° C. for 30 seconds. To ensure mechanically robust, yet porous arrays of IDE segments, in-situ amorphous carbon infiltration into the CNT forest of the sensor 300 shown in FIG. 3D was performed for 3 min by flowing hydrogen and ethylene (311 sccm and 193 sccm, respectively) at 900° C.

After amorphous carbon infiltration, in order to remove a carbon floor between the segments of the IDE, which is deposited in a conformal fashion across the entire IDE sensor 300 and silicon wafer 300 surface during the deposition of the amorphous carbon, an oxygen ($O_2$) plasma etch was performed for 45 seconds at 250 W and 300 mTorr.

As shown in FIG. 3D (e.g., by the inset 335), after fabrication of the IDEs of the sensor 300 (as shown in FIGS. 3A-3D and described), an anti-CIP2A antibody (Ab) 340 was attached to (bonded to, immobilized on, etc.) the surface the 3D VANTA IDE sensor 300 and then used to capture CIP2A antigen (Ag) 343.

Activity of the Ag and Ab pair of FIG. 3E was tested prior to functionalizing the electrodes of the sensor 300 using immunoblotting. This activity was tested using VANTA IDEs that were prepared using the following process. The VANATS IDEs were cleaned in a 0.1 molar (M) 2-(N-morpholino) ethanesulfonic acid (MES) buffer for 10 mins, followed by incubation in a solution of 0.4 M N-(3-Dimethylaminopropyl)-N'-ethylcarbodiimide (EDC) and 0.1 M N-Hydroxy succinimide (NHS) prepared in a 0.1 M MES buffer for 1 hour. The VANTA IDEs were then washed in phosphate-buffered saline (PBS) and then placed under a gentle stream of nitrogen gas to remove excess amounts of liquid and non-specifically absorbed protein.

Next, the VANTA IDEs were incubated overnight with a 1:100, 5 microgram per mL (μg/mL) dilution of CIP2A antibody. The reaction was quenched with 1.0 M ethanolamine to block unbound carboxyl groups. Finally, the IDEs were blocked in 2% Bis(trimethylsilyl)acetamide (BSA) for 1 hour to reduce non-specific binding of CIP2A antigen to bare areas of the VANTA IDEs or the corresponding substrate during electrochemical sensing. The functionalized (biofunctionalized) VANTA IDEs were washed in PBS and placed under a nitrogen stream that was sufficiently strong to remove excess water, but sufficiently weak to leave the biofunctionalized surface unharmed as verified with subsequent fluorescence microscopy and electrochemical CIP2A biosensing.

For sensing CIP2A, 20 microliters (μL) of Ag (e.g., at the concentrations corresponding with FIGS. 9A-9D) was placed on the VANTA IDEs and incubated for 30 minutes. EIS measurements were then performed in 5 millimolar (mM) ferro/ferricyanide solution, the results of which are shown in FIGS. 9A-9D and discussed further below.

By way of background, the protein CIP2A is comprised of 905 amino acids and has a molecular mass and approximate radius of 102 kilodaltons (kDa) and 3 nm respectively. The amine terminated CIP2A antibody has an approximate size of 90 kDa and is covalently bound to the superficial carboxyl groups found on the CNT surface via EDC/NHS chemistry. Accordingly, the immobilized antibody can extend approximately 3 nm outward from the surface of the CNTs of the VANTA IDEs. To put these dimensions into perspective, the amorphous carbon coated CNTs within the VANTA IDEs have an approximate width of 100 nm, while the width of one of the IDE electrode segments (e.g., the electrodes 212 or 222 in FIG. 2B) can be 25 μm.

Referring again to FIG. 3E, prior to electrochemical sensing tests (e.g., EIS measurements) in the active solution, the electrical resistances of the two electrodes of the VANTA IDE sensor 300 were measured with 10-20Ω resistance being detected across a contact pad (corner to corner, such as from the contact pad 216 to the contact pad 226 in FIG. 2). The VANTA IDEs were next treated with $O_2$ plasma to remove the carbon floor between the segments of the IDE, the carbon floor being created from the amorphous carbon deposition process. After this $O_2$ plasma etch, an infinitely high resistance between the two distinct segment (finger) combs (e.g., the two IDEs) was observed. That is, no electrical shorting between the two IDEs of the sensor 300 was detected.

Figure 3F:
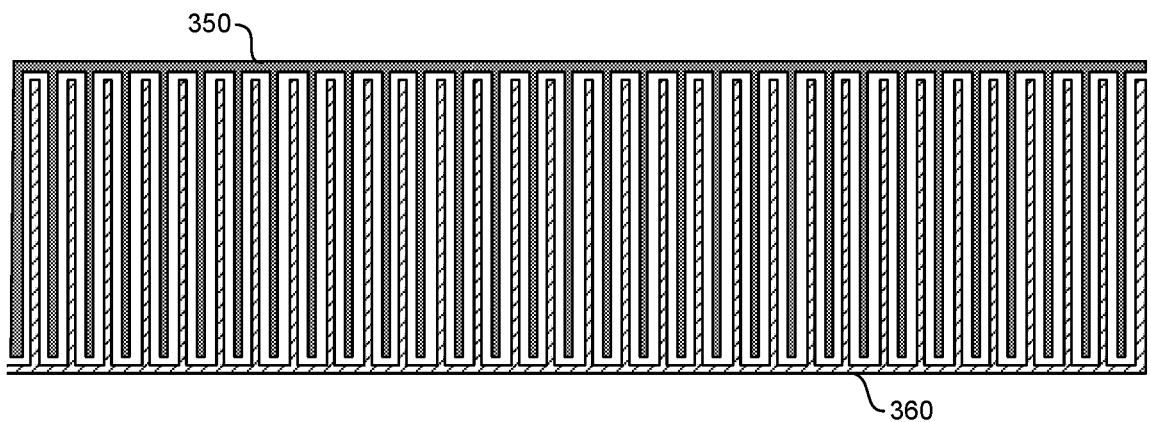
FIGS. 3F and 3G are diagrams illustrating plan views of respective interdigitated (carbon nanotube array) electrodes that can be implemented in an immunosensor.
Figure 3G:
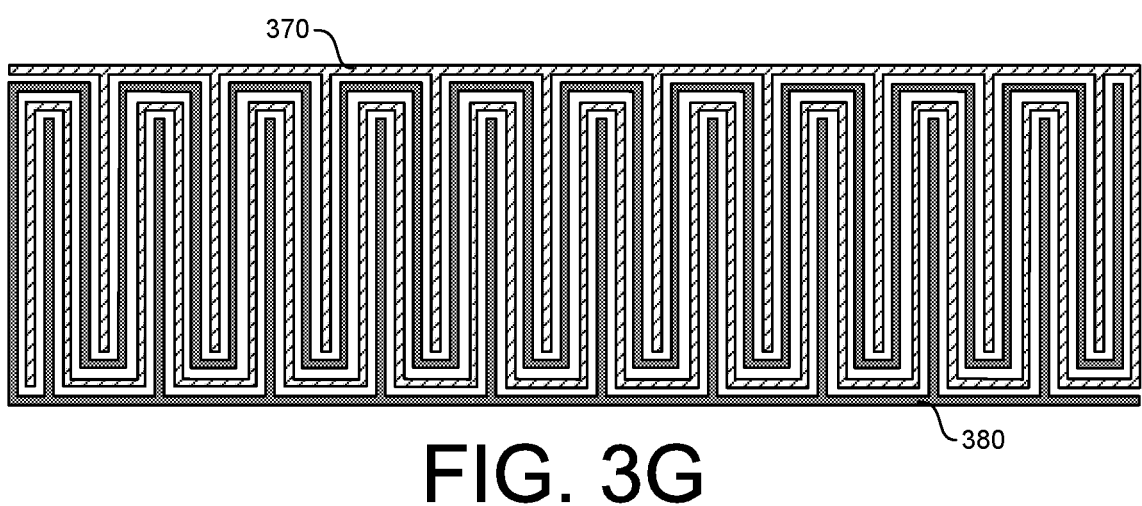

Additionally, in some implementations, the $O_2$ plasma treatment (e.g., oxygen etching, plasma etching, etc.) can also enhance the surface wettability of the VANTA IDEs, so that a static contact angle changes from ~110° (e.g., hydrophobic) to ~69° (e.g., hydrophilic). Such an oxygenated, hydrophilic surface can improve the penetration of aqueous solutions into the porous VANTA IDE structure and, can consequently enhance biofunctionalization and biosensor sensitivity. In some implementations, performing a bake process on the IDE can increase hydrophobicity of the IDE. For instance, a bake process (e.g., above an ambient room temperature) can be performed on the IDE in a vacuum (e.g. at a pressure that is less than atmospheric pressure). FIGS. 3F and 3G are diagrams illustrating plan views of respective interdigitated (carbon nanotube array) electrodes that can be implemented in an immunosensor.

FIGS. 3F and 3G are diagrams illustrating plan views of respective interdigitated (carbon nanotube array) electrodes that can be implemented in an immunosensor. FIG. 3F illustrates an IDE that includes a first electrode 350, and a second electrode 360 that includes segments (fingers) that are interdigitated (interleaved, interwoven, interspersed, etc.) with segments (fingers) of the electrode 360. FIG. 3G illustrates an IDE that includes a first electrode 370 (having segments arranged in a serpentine pattern and segments arranged as fingers) and a second electrode 380 370 (having segments arranged in a serpentine pattern and segments arranged as fingers), where the electrode segments of the electrode 380 are interdigitated (interleaved, interwoven, interspersed, etc.) with the electrode segments of the electrode 370. In some implementations, combinations of the arrangements of the IDEs described herein, or other arrangements are possible.

Figure 4:
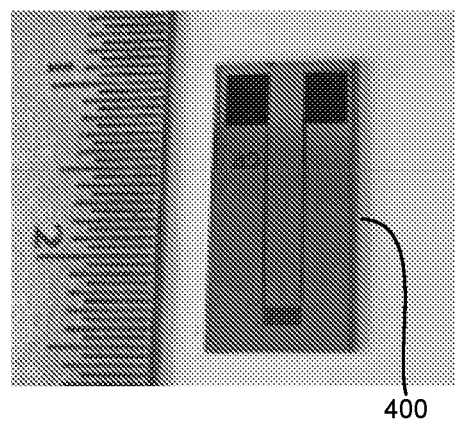
FIG. 4 is a diagram illustrating a scale of an immunosensor, such as the immunosensors of FIGS. 2 and 3.

FIG. 4 is a diagram illustrating a scale of an immunosensor 400, such as the immunosensors of FIGS. 2 and 3. In FIG. 4, general dimensions of 3D VANTA IDE sensors are shown by a diagram of a 3D VANTA IDE sensor 400 on a corresponding substrate shown next to ruler, where the dimensions on the ruler are shown in centimeters (cm), with a vertical dimension of the sensor 400 in FIG. 4 being approximately 1.5 cm.

Figure 5A:
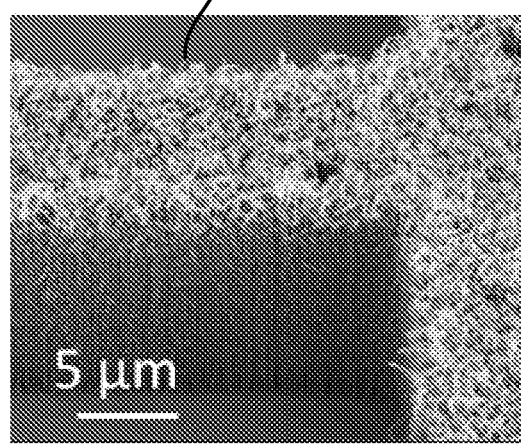
FIGS. 5A and 5B are scanning electron microscope images of a patterned VANTA that can be included in an immunosensor at different magnification levels.
Figure 5B:
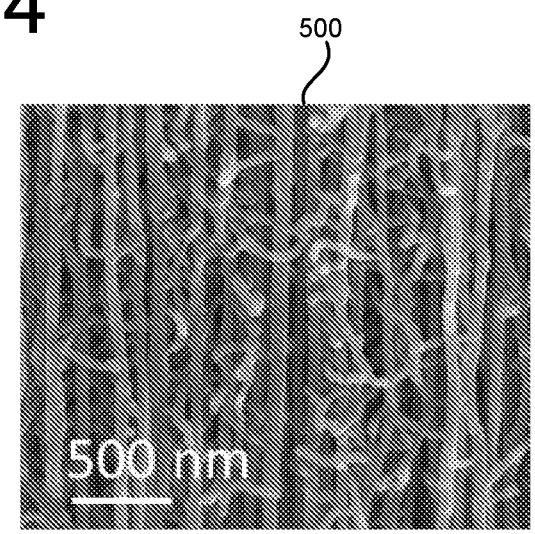

FIGS. 5A and 5B are diagrams of scanning electron microscope images of a patterned 3D VANTA 500 that can be included in an immunosensor, shown at different magnification levels. The image in FIG. 5B is at a magnification of 10 times that of the image in FIG. 5A. The highly porous and defect-rich nature of the VANTA 500 structures shown in the images of FIGS. 5A and 5B. In the high-resolution image of FIG. 5B, individual nanotubes are identifiable, as well as carbon matrix binding along a sidewall of the VANTA 500. The entanglement of amorphous carbon and the VANTA 500 results in a mechanically stable structure during subsequent biofunctionalization and electrochemical sensing.

Figure 6:
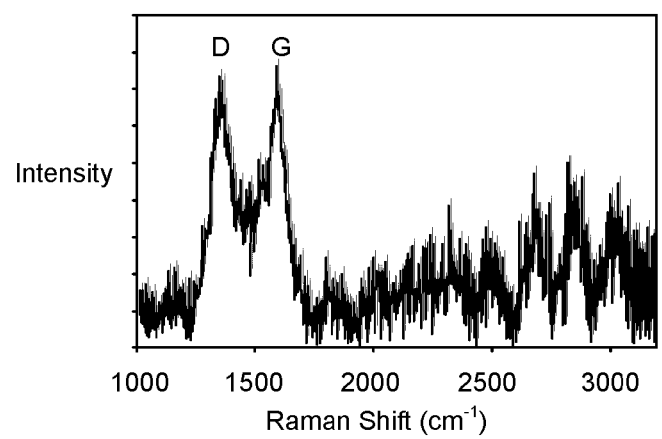
FIG. 6 is a graph illustrating Raman spectroscopy results for an immunosensor, such as the immunosensors of FIGS. 2 and 3.

FIG. 6 is a graph illustrating Raman spectroscopy results for a VANTA IDE, such as the VANTA IDEs described herein. The Raman spectroscopy results of FIG. 6 illustrate characteristic CNT D and G spectrographic peaks. For instance, as shown in FIG. 6, the Raman spectra revealed a G-band (1590 cm$^{-1}$), and 2D-band (2700 cm$^{-1}$), which correlates well with spectra commonly associated with arrays of CNTs. Moreover, the presence of the D-band (1350 cm$^{-1}$) and its high intensity relative to the G-peak intensity ($I_D/I_G$~0.94) indicates a high quantity of superficial carbon defects. Such carbon defects are indicative of edge plane sites that have been shown to increase heterogeneous charge transfer during electrochemical sensing and deposition, which can improve electrochemical sensor accuracy or sensitivity.

The Raman spectrum measurements of the VANTA IDEs illustrated in FIG. 6 were made using a spectrometer with a 488 nm excitation source at a 20 milliwatt (mW) laser power. A 20× objective lens was used in a microscope for data acquisition in a backscattered configuration. There were 5 acquisitions of 20 s each, and the acquired spectra were processed using software to remove inherent fluorescence using a modified polynomial baseline reduction method.

Figure 7A:
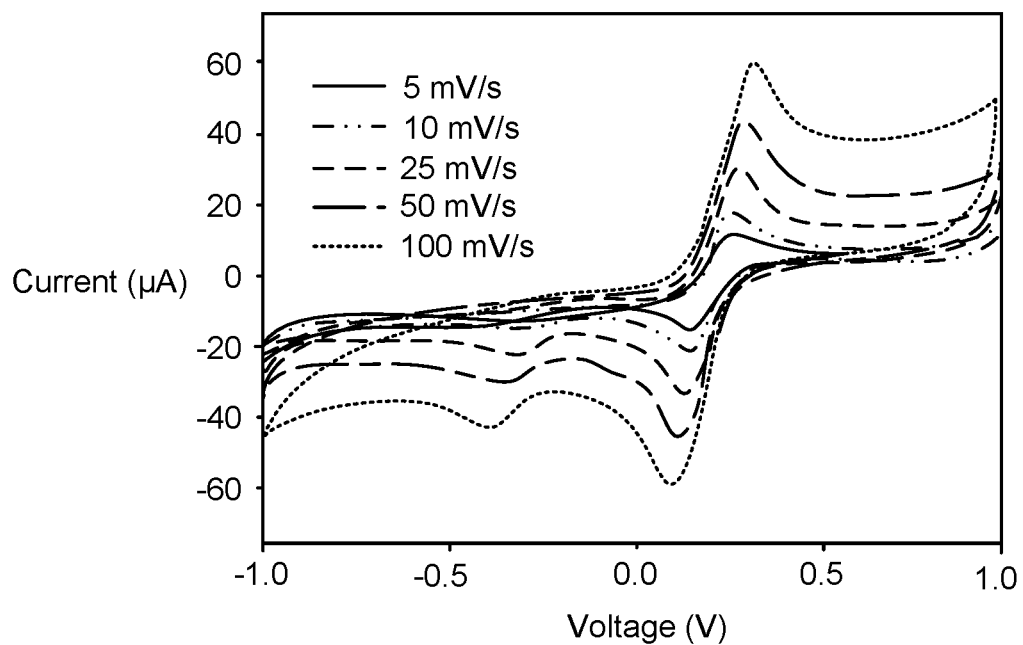
FIGS. 7A-7F are graphs illustrating various electrochemical testing results for an immunosensor, such as the immunosensors of FIGS. 2 and 3.
Figure 7B:
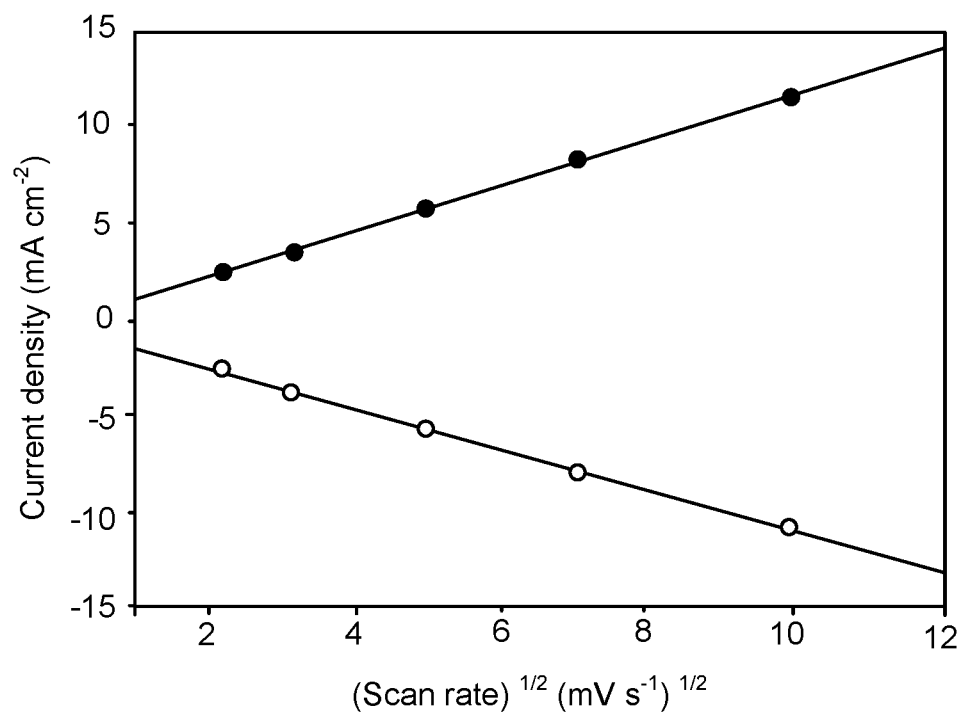
Figure 7C:
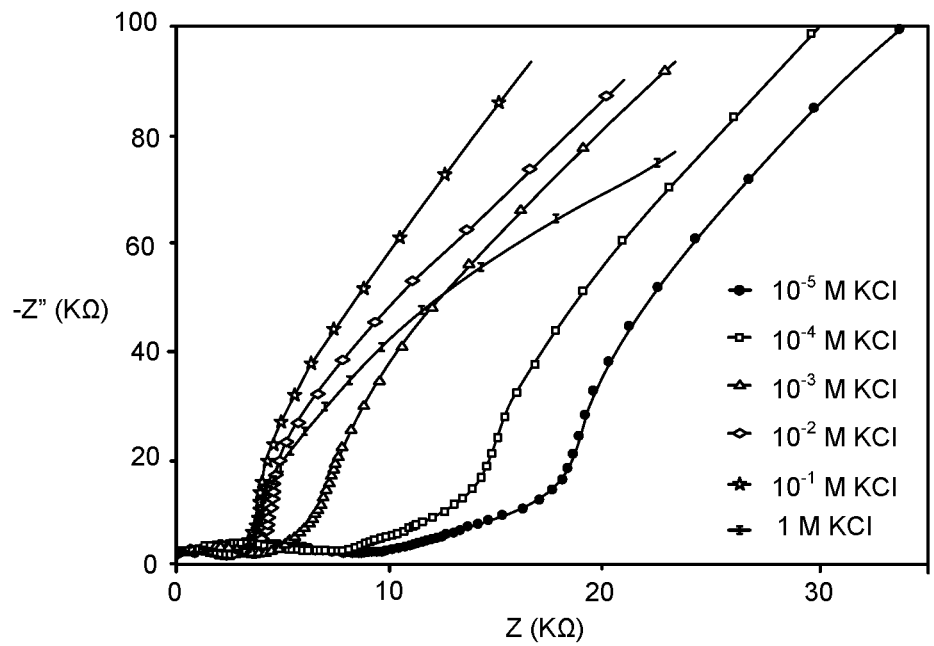
Figure 7D:
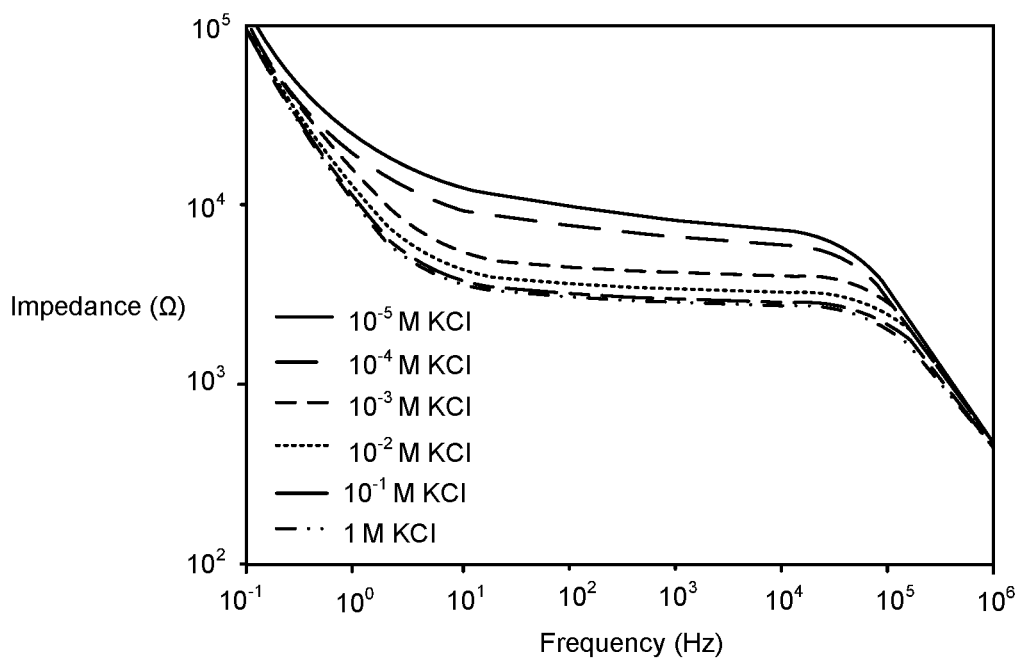
Figure 7E:
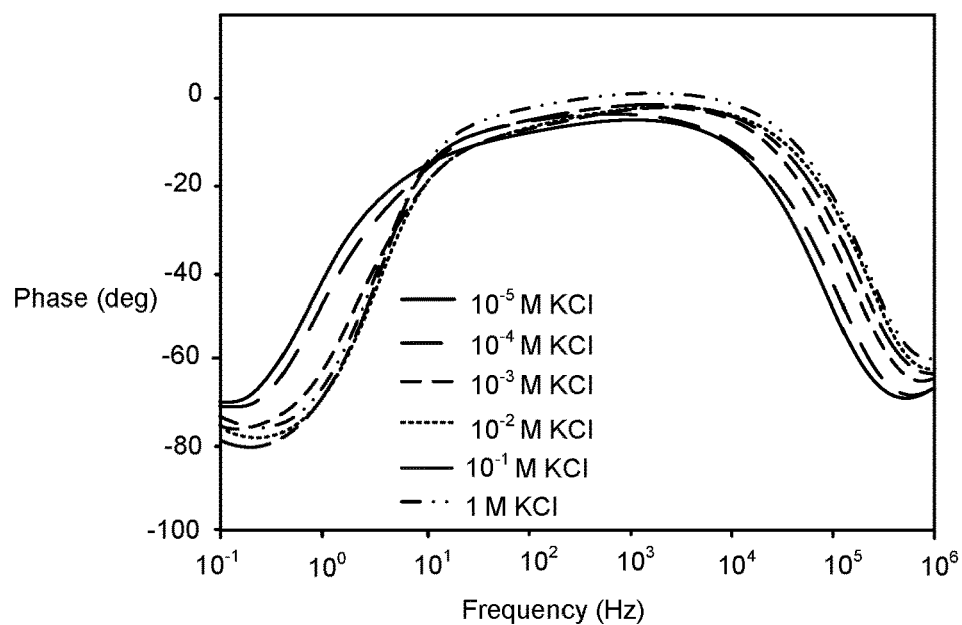
Figure 7F:
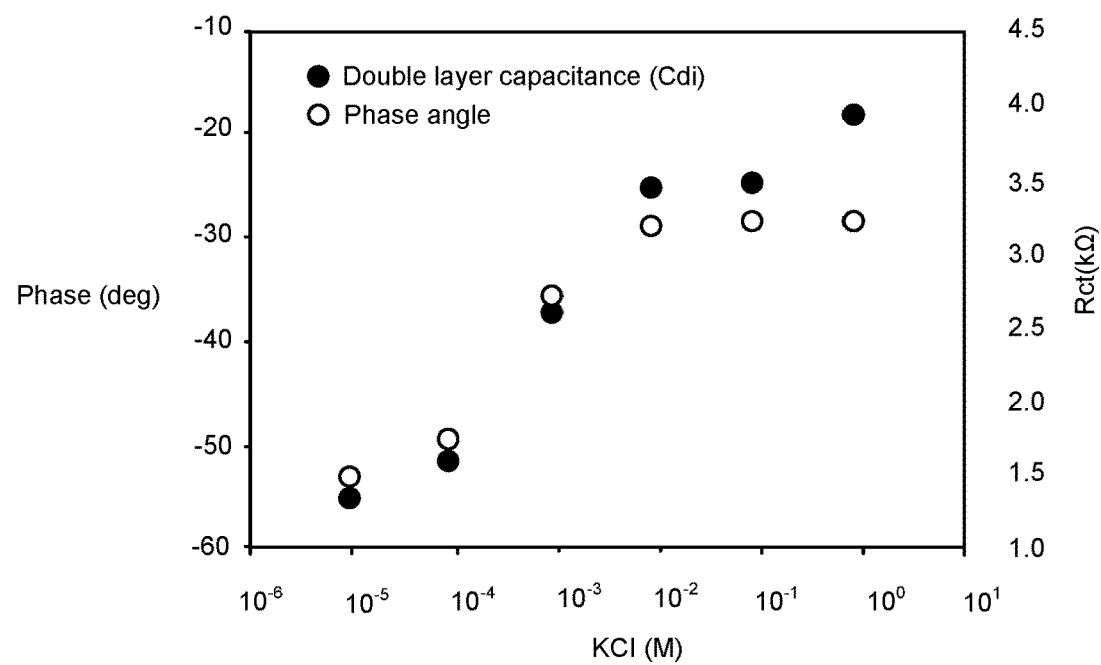

FIGS. 7A-7F are graphs illustrating various electrochemical testing (characterization) results for an immunosensor (e.g., 3D VANTA IDE devices), such as the immunosensors of FIGS. 2 and 3. For instance, FIG. 7A illustrates cyclic voltammetry (CV) data at scan rates of 10, 25, 50, 75, and 100 mV/s. FIG. 7B illustrates current density vs. the square root of the scan rate data. FIGS. 7C, 7D and 7E illustrate data illustrate characterization of 3D VANTA IDEs by sensing various concentrations of KCl. Specifically, FIG. 7C illustrates resulting Nyquist plots, FIG. 7D shows corresponding impedance data, and FIG. 7E illustrates phase change vs. frequency. FIG. 7F illustrates data for double layer capacitance and phase angle at 100 KHz versus KCl concentration.

The data shown in FIGS. 7A-7F illustrates characterization of electrochemical reactivity of 3D VANTA IDEs (such as described herein), where the characterization was performed with ferricyanide cyclic voltammetry (CV) and EIS measurements. The electrochemical characterization data of FIGS. 7A-7F was collected using the following compounds: (1) potassium ferrocyanide; (2) potassium ferricyanide; (3) N-(3-Dimethylaminopropyl)-N'-ethylcarbodiimide (EDC), N-hydroxy succinimide (NETS); (4) ethanolamine; (5) a fluorescein isothiocyante tagged (FITC-tagged) anti-mouse secondary Ab; (6) CIP2A Ag (0.063 µg/µl); (7) mouse monoclonal Ab against CIP2A (0.5 mg/mL); and (8) 2-(N-morpholino) ethanesulfonic acid (MEMS buffer, 0.5 M, pH=6.0). Further, the electrochemical characterization data of FIGS. 7A-7F was collected, and corresponding sensing experiments were performed using: (1) a potentiostat; (2) an Ag/AgCl reference electrode and (3) a Pt wire counter electrode within a ferricyanide solution (5 mM Fe $(CN)_6^{3-/4-}$), e.g., for CV measurements.

For the characterization data of FIGS. 7A-7F, after functionalization with the CIP2A Ab, corresponding VANTA IDEs were operated in a 2-electrode set-up without the use of an external reference electrode, and with an EIS sensing modality. CIP2A calibration curves were acquired by using a standard addition method (e.g., subsequent concentration of Ag was added to the same functionalized VANTA IDE) with EIS. CIP2A sensing was carried out within 10 µL of PBS and 10 µL of human saliva supernatant. A healthy participant (e.g., without cancer) was required not to their brush teeth, drink hot liquids, or eat food in the morning before providing saliva samples. Whole saliva (10 ml) was collected by passive human drool into a 15 ml plastic tube, and the supernatant was acquired by centrifuging the saliva at a speed of 1000 RPM for 30 min and then carefully removing the top of the liquid, e.g., the supernatant, via pipette extraction from the solid phases. The supernatant was then filtered by a 0.4 µm syringe filter and used for the characterization testing.

As shown in FIG. 7A, well-defined anodic and cathodic peak currents ($I_p$) were obtained across a range of scan rates (5, 10, 25, 50, and 100 mV s$^{-1}$) due to the ferricyanide ($Fe^{3+}/Fe^{2+}$) redox couple. As shown in FIG. 7B, these peak currents display a linear relationship, indicating reversible behavior, when plotted against the square-root of the voltage scan (Randles-Sevcik plot).

It is noted that a minor redox peak appears near −0.41 V due to a $Fe/Fe^{2+}$ redox couple (FIG. 7A). This redox couple is present in the electrode due to the use of the Fe metal catalyst that seeds the growth of CNTs during the CVD synthesis (growth) process, as was discussed above. Moreover, the peak-to-peak separation ($\Delta E_p$) values range from 0.10 V to 0.21 V across the acquired scan rates (FIG. 7A). Such low $\Delta E_p$ values are indicative of fast and reversible heterogeneous electron charge transfer at room temperature and are significantly lower to ferricyanide electrochemistry electron transfer rates acquired from the basal planes of highly oriented pyrolytic graphite ($\Delta E_p$ 630 mV). These $\Delta E_p$ values compare favorably with similar CNT-based electrodes where aligned MWCNTs electrodes, horizontally oriented SWCNT paper, and vertically oriented SWCNT arrays report $\Delta E_p$ values of 0.23 V, 0.096 mV, and 0.090 mV respectively.

The effective electroactive surface area (A≈0.00513 mm$^2$) of the VANTAs used for the characterization of FIGS. 7A-7F was calculated by incorporating the recorded $I_p$ values into the Randles-Sevcik equation, Equation 1 below:

$$I_p = (2.69 \times 10^5) n^{3/2} v^{1/2} D^{1/2} CA \quad \text{(Equation 1)}$$

where n is the number of electrons transferred by the $Fe^{3+}/Fe^{2+}$ redox couple (n=1), v is the scan rate (v=100 mV/s), D is the diffusion coefficient (D=7.20×10$^{-6}$ cm$^2$/s), and C is the analyte concentration (C=5 mM). An electroactive surface area of this value results in approximate 1% active sites (e.g., the surface area where heterogeneous charge transport occurs; active site is the ratio between electroactive surface area and geometric area) for the $Fe^{3+}/Fe^{2+}$ redox couple estimated during ferricyanide cyclic voltammetry (CV) at a scan rate of 50 mV/s. Such values are greater than previous sensors, which demonstrate approximately 0.4% active sites. Thus, the porous nature of the VANTA IDEs demonstrates significantly increased electroactive surface area, as compared with a conventional solid or planar sensor, and provides more carbon-carbon defects, or active sites than conventional CNT electrodes.

To further demonstrate the impedimetric response of the VANTA IDEs, EIS ferricyanide measurements were conducted in the frequency range from 0.1 Hz to 1 MHz using increased concentrations of KCl (from 1.0 µM to 1.0 M KCl), for which the collected characterization data is illustrated in FIGS. 7D and 7E. These faradaic EIS measurements can be represented as a three-component equivalent circuit (e.g., a 3-electrode potentiometric set-up with a reference electrode-the sensing modality used to electrochemically characterize the VANTA IDEs) where $C_{dl}$ is the double layer capacitance, $R_s$ is ionic resistance from electrolyte, and $C_{dl}$ is the dielectric capacitance from the electrolyte. At lower frequencies (0.1 Hz to 10 Hz), $C_{dl}$ governs the overall impedance change, from which lower KCl concentration leads to a higher amplitude and lower phase shift. At the intermediate frequency region (10 Hz to 10 KHz), the conduction/resistance of ions in solution, $R_{sol}$, dominates the impedance. At higher frequencies (10 KHz to 1 MHz), the dielectric capacitance supersedes the impedance, resulting in a higher phase shift at lower KCl concentrations. The results shown in FIGS. 7D and 7E indicate how each component of VANTA IDEs respond to the change of KCl concentrations in the electrolyte.

In addition, as shown in FIG. 7F, the VANTA IDEs tested displayed increased sensitivity to KCl concentrations changes as compared to conventional planar sensors under similar conditions, corroborating the high sensitivity of the 3D VANTA IDEs in subsequent immunosensing.

Figure 8:
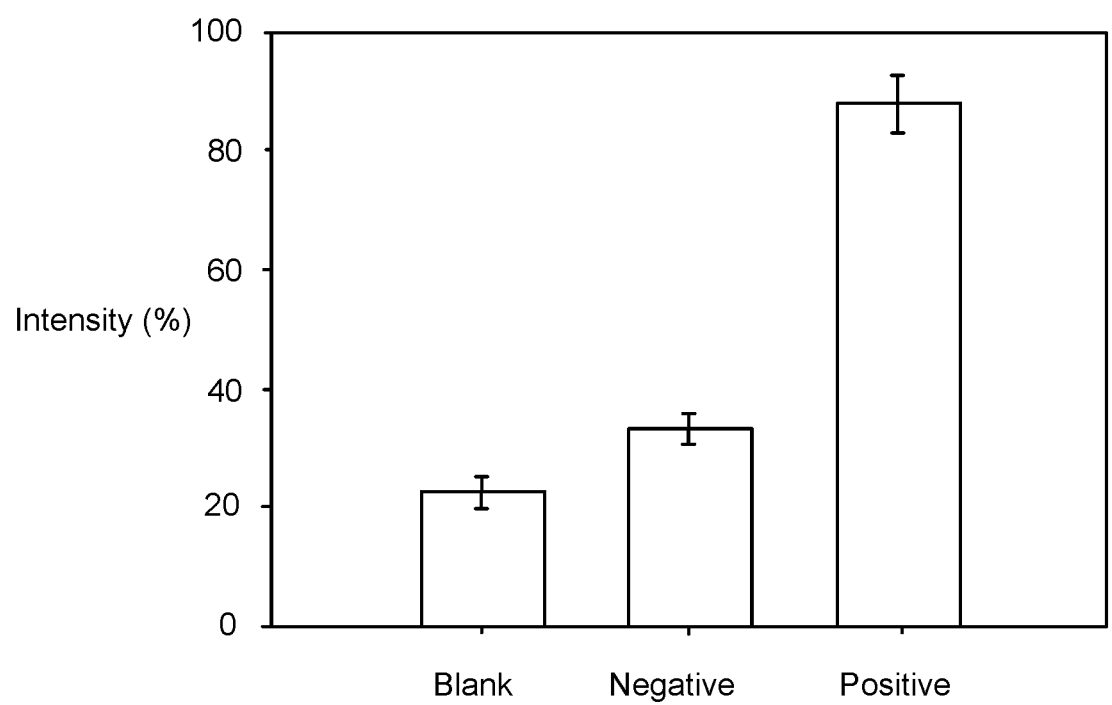
FIG. 8 is a histogram showing fluorescence results for a VANATA IDE immunosensor.

FIG. 8 is a histogram showing fluorescence results for a 3D VANATA IDE immunosensor. The fluorescence results shown in FIG. 8 represent data from fluorescence monitoring of Ab-Ag binding to VANTA IDEs. Such data included (1) fluorescence emitted from the VANTA IDEs functionalized with FITC-tagged secondary Ab only (e.g., fluorescence OFF), and (2) with both primary CIP2A antibodies and FITC tagged secondary antibodies (e.g., fluorescence ON). The histogram of FIG. 8 is a comparative histogram illustrating relative fluorescence emissions from a blank VANTA IDE, a negative control VANTA IDE, and a positive control VANTA IDEs, respectively.

Prior to immunosensing, immobilization of the anti-CIP2A Ab onto the VANTA IDEs was confirmed via fluorescence imaging (e.g., corresponding with the data in the histogram of FIG. 8). To visualize the successful loading of Ab, a FITC-tagged, secondary Ab was used to bind the primary Ab, thus relating fluorescence to the amount of anti-CIP2A Ab on the VANTA IDE surface (positive control in FIG. 8).

Referring still to the histogram of FIG. 8, three VANTA IDEs were prepared for fluorescence spectroscopy measurements as follows: (1) a positive control electrode was biofunctionalized using the approach described herein; (2) a negative control electrode was prepared in a similar fashion as the positive control electrode, but without the use of primary Ab; and (3) a third electrode was a non-functionalized bare VANTA IDE (e.g., a blank control). Next, 10 µL of 1:200 dilution of anti-mouse IgG-FITC Ab produced in goat were placed on the positive and negative control IDEs, respectively, and incubated for 1 hour. The negative control was applied to show there was no binding between the BSA blocked electrode and the secondary Ab, while the blank control demonstrated that the non-functionalized VANTA IDE did not display autofluorescence. FITC-fluorescence was used to display average intensity values (obtained from image analysis software) with standard deviation error bars (for n=3 samples), such as shown in FIG. 8.

To evaluate non-specific binding of the FITC-tagged Ab with the VANTA IDE surface, the negative control was performed in which the FITC-tagged Ab was incubated with the VANTA IDEs in the absence of primary Ab surface functionalization. As shown in FIG. 8, the negative control experiment resulted in negligible VANTA fluorescent labeling as compared to the positive control. As shown in FIG. 8, the positive control experiment did result in measurable VANTA fluorescence labeling. As noted above, results for the positive and negative Ab loading experiments are illustrated in FIG. 8, where the histogram compares the FITC-fluorescence intensities (%) of the negative and positive controls to samples without any biofunctionalization (e.g., blanks). This result demonstrates successful loading of Ab onto the surface of the VANTA IDEs.

FIGS. 9A-9D are graphs illustrating calibration data for a VANTA IDE immunosensor for detecting an oncoprotein, e.g., the CIP2A oncoprotein. That is, FIGS. 9A-9D are calibration plots for 3D VANTA IDE electrochemical sensors that are functionalized with the anti-CIP2A Ab.

Figure 9A:
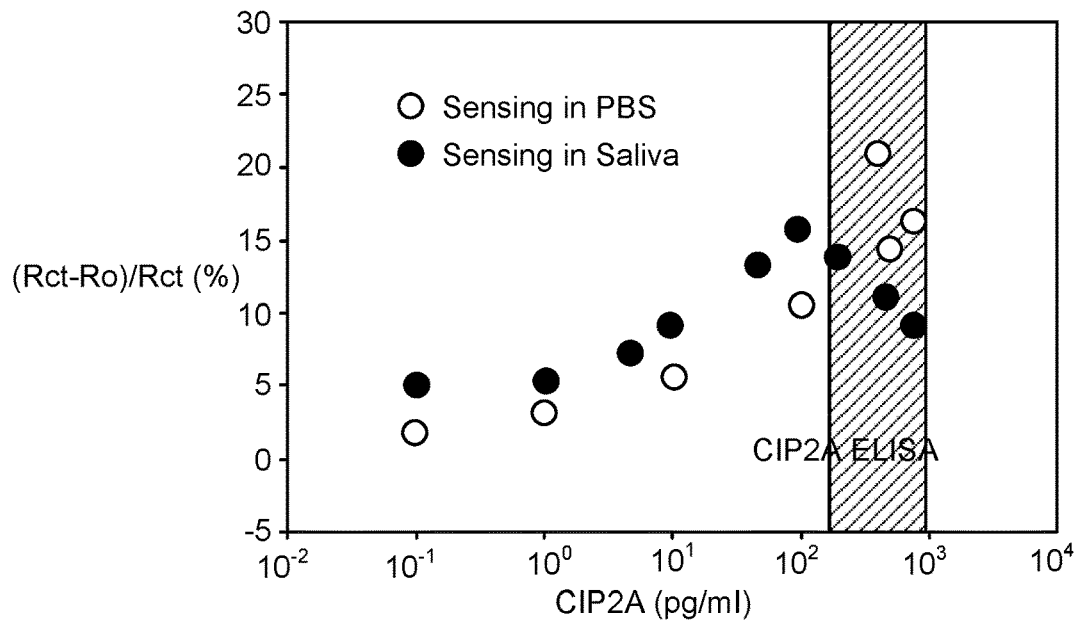
FIGS. 9A-9D are graphs illustrating calibration data for a VANTA IDE immunosensor for detecting an oncoprotein.
Figure 9B:
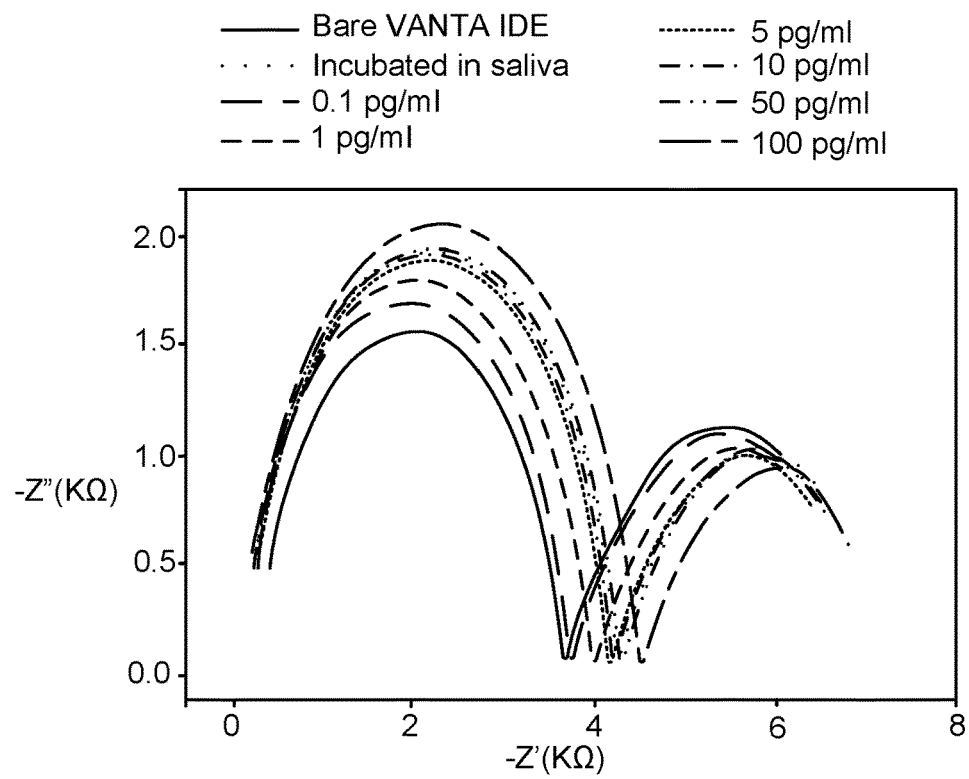
Figure 9C:
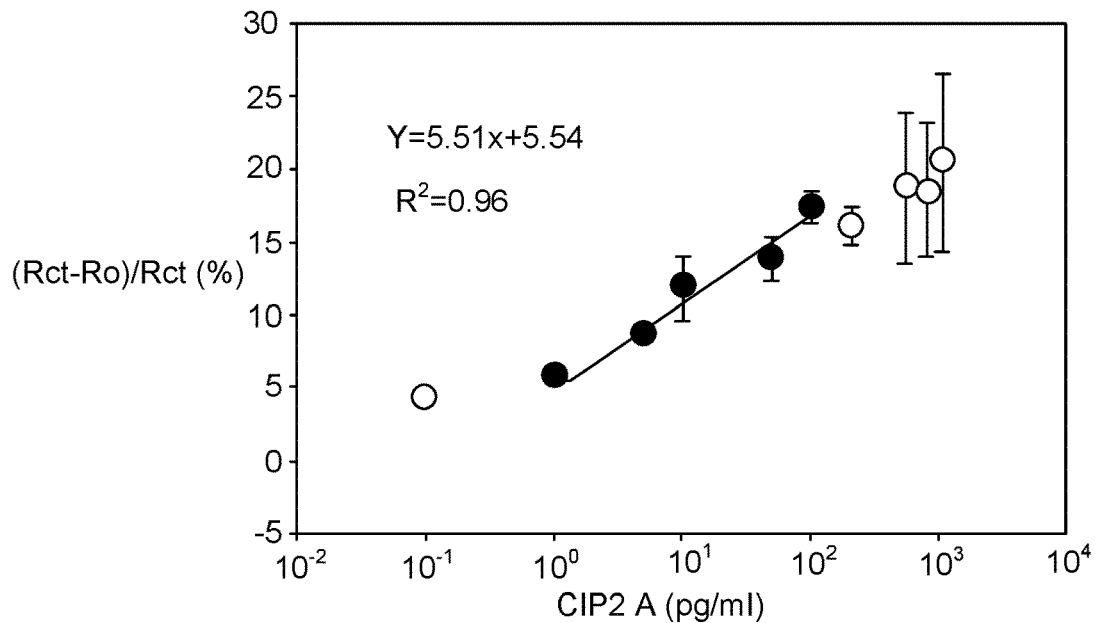
Figure 9D:
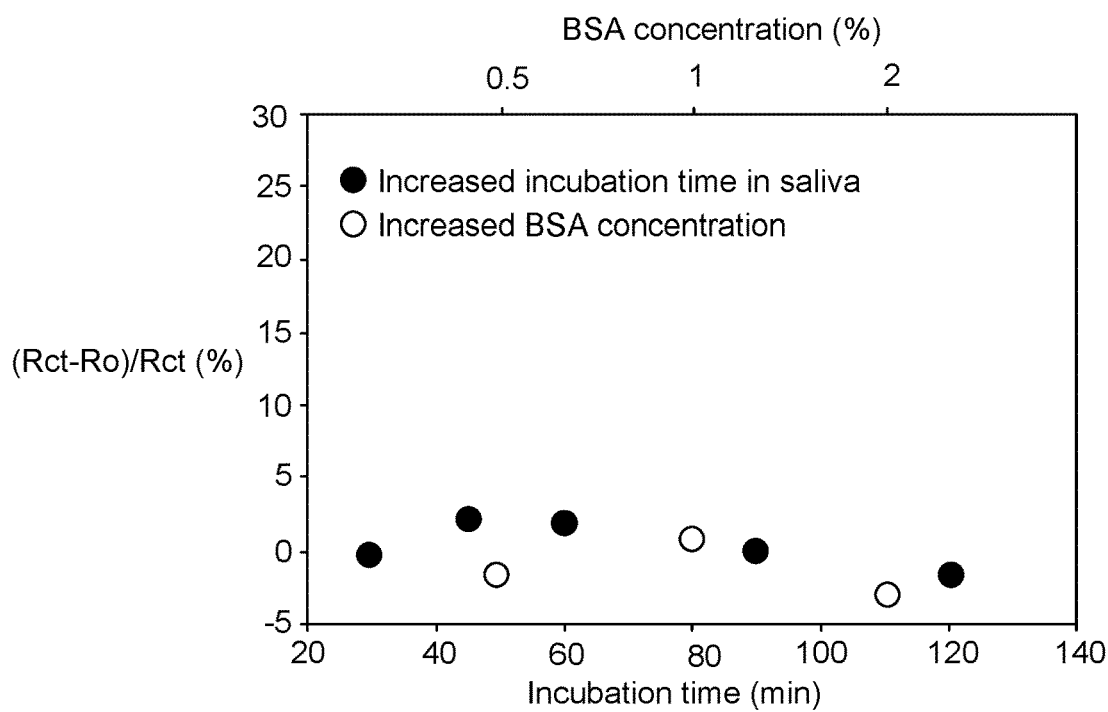

FIG. 9A illustrates data for functionalized VANTA IDEs tested in PBS and saliva with sequential CIP2A concentration increases of 0.1, 1, 10, 100, 200, 400, 500, and 750 pg/ml in PBS and 0.1, 1, 5, 10, 50, 100, 200, 500, 750 pg/ml in saliva. In FIG. 9A, the first data points were acquired as a baseline without CIP2A. The shaded region in FIG. 9A illustrates a sensing range of a typical human CIP2A ELISA kit. FIG. 9B illustrates CIP2A Nyquist plots acquired in (using) a saliva supernatant. FIG. 9C, illustrates CIP2A calibration plots of anti-CIP2A Ab functionalized VANTA IDEs tested in saliva. For the data shown in FIG. 9C, four functionalized VANTA IDEs were tested, and standard deviation bars are shown to indicate the repeatability and reproducibility (e.g., with n=4). Regression analysis of the data shown in FIG. 9C revealed that the linear sensing range of such VANTA IDE sensors is between 1 and 100 pg/ml). FIG. 9D illustrates data for anti-CIP2A Ab functionalized VANTA IDEs that were also tested in saliva, with increased incubation times and increased BSA concentrations.

For the data illustrating immunosensing of CIP2A shown in FIGS. 9A-9D, as briefly noted above, VANTA IDEs were functionalized with anti-CIP2A Ab and then incubated with increasing concentrations of CIP2A Ag. EIS measurements demonstrated that the resulting VANTA IDE immunosensors were capable of sensing CIP2A across a wide concentration range from 5 pg/mL to 400 pg/mL in phosphate buffer solution and from 1-100 pg/ml in saliva supernatant, as shown in FIG. 9A.

As also noted above, FIG. 9B illustrates a Nyquist plot of impedance measurements corresponding with the detection of CIP2A in saliva supernatant. It is noted that the magnitude of each trace on the Nyquist plot of FIG. 9B (e.g., the radius of the first half circle) increases with increasing CIP2A concentration. The normalized percent change of charge transfer resistance, $R_{ct}$, was calculated and plotted versus concentrations of CIP2A, with that data being illustrated in FIGS. 9A, 9C and 9D. The linear CIP2A sensing ranges of the VANTA IDE immunosensor noted above (e.g., 5-400 pg/ml in PBS and 1-100 pg/ml in saliva) were calculated using regression analysis of the normalized charge transfer resistance versus the functionalized CIP2A concentration plots.

As illustrated by a comparison of the VANTA IDE sensor data and the shaded area in FIG. 9A, which indicates the sensing range of a typical human CIP2A ELISA kit (0.156-10 ng/mL), FIG. 9A demonstrates that the VANTA IDE sensors demonstrate higher sensitivity and a lower sensing range (e.g., lower concentration detection limit) in both PBS and saliva supernatants than the corresponding ELISA test kits.

Functionalized VANTA IDEs were also tested in saliva with increased incubation times (30, 45, 60, 90, and 120 mins) and increased BSA concentrations (0.5%, 1% and 2%), from which the impedance measurements indicated minimal interference/non-specific adsorption from BSA proteins and high stability in the complex saliva matrix, for which the collected data is shown in FIG. 9D. These experiments show that the biofunctionalized VANTA IDEs are relatively resilient to non-specific adsorption of protein and selective to CIP2A with negligible interference from electroactive species found endogenously in saliva supernatant. This indicates the feasibility of applying VANTA IDEs toward early stage detection of oral cancers in actual patient (turbid) saliva samples.

Figure 10A:
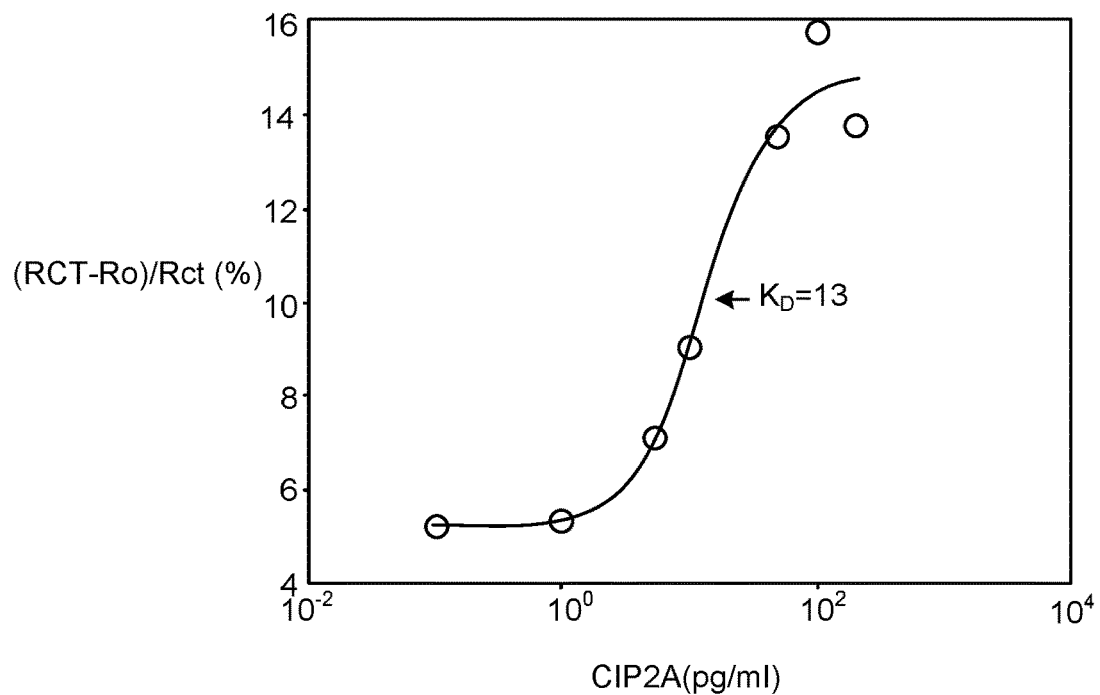
FIGS. 10A-10B are graphs calibration curves for sensing an oncoprotein using a VANTA IDE immunosensor.
Figure 10B:
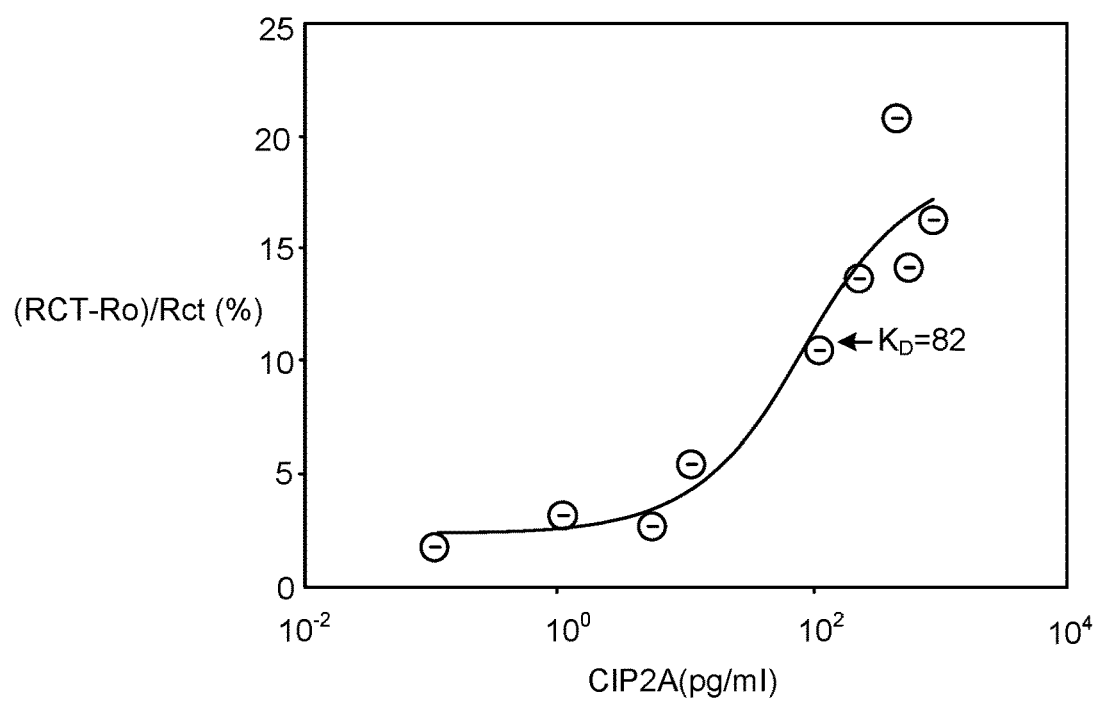

FIGS. 10A-10B are graphs illustrating calibration curves for sensing an oncoprotein (e.g., the CIP2A oncoprotein) using a VANTA IDE immunosensor. For instance, the calibration curve of FIG. 10A corresponds with CIP2A sensing in saliva and was fit using non-linear regression analysis using the Hill Equation. Likewise, the calibration curve of FIG. 10B corresponds with CIP2A sensing in PBS and was also fit using non-linear regression analysis using the Hill Equation (Equation 2 below for FIG. 10 A, and Equation 3 below for FIG. 10B). FIG. 10A illustrates that an estimated $K_D$ value (for sensing in saliva) is 13 pg/ml with a coefficient of 1.62, while FIG. 10B illustrates that an estimated $K_D$ value (for sensing in PBS) is 82 pg/ml with a coefficient of 0.98, which is illustrative of the difference in range of sensing activity between the two sample mediums.

In FIGS. 10A and 10B, the linear regions were utilized to determine detection limits (e.g., concentration detection lower limits) using 3σ guidelines. The resultant curve fit equations (Equations 2 and 3) are given below, where θ is the fraction of occupied Ab that Ag can potentially bind to, Ag is the concentration of Ag, and $K_D$ is the dissociation constant discussed above.

$$\theta \text{ (in } PBS\text{)} = \frac{Ag^{0.98}}{K_D + Ag^{0.98}} \quad \text{(Equation 2)}$$

$$\theta \text{ (in saliva)} = \frac{Ag^{1.62}}{K_D + Ag^{1.62}} \quad \text{(Equation 3)}$$

These sigmoidal curve fits indicate the VANTA IDE biosensor performance characteristics, and enable a better understanding of the binding activity between Ab (anti-CIP2A) and Ag (CIP2A) within different sensing environments (e.g., saliva and PBS). As indicated above, the PBS sensing data resulted in a $K_D$ value of 82 pg/ml with a Hill coefficient of 0.98 (or ~1), which is indicative of independent binding. However, in saliva, the $K_D$ value was determined to be 13 pg/ml (indicating higher Ab affinity to Ag than in PBS), with a Hill coefficient of 1.62 (which is indicative of slight positive cooperative binding).

The primary governing factors that control Ab-Ag binding within an aqueous medium are the pH, salt type, temperature, and ionic strength of the given medium. In the case of this particular characterization, the decreased $K_D$ value or increased antibody affinity to CIP2A Ag and higher level of cooperative binding displayed during biosensing in the saliva supernatant matrix could be a result of pH, salt type, and ionic strength in the saliva solution than in PBS. It is noted that saliva supernatant was used in these experiments, so that non-specific absorption from high molecular weight proteins and cellular matter (which could reduce biosensor sensitivity) was reduced, as these particles were removed during the centrifugation process.

The calibration curve fits in FIGS. 10A and 10B include an initial stationary stage, a linear sensing stage, and a saturation stage. Subsequently the CIP2A detection limit in both PBS and saliva, 4.69 pg/mL and 0.24 pg/ml respectively, were acquired from the intersection between the linear trend line of the Hill Equation calibration fit and the x-axis (using 3 times the standard deviation of the background signal acquired before CIP2A spiking or 3σ guidelines), such as illustrated in FIGS. 9A and 9C.

Figure 11A:
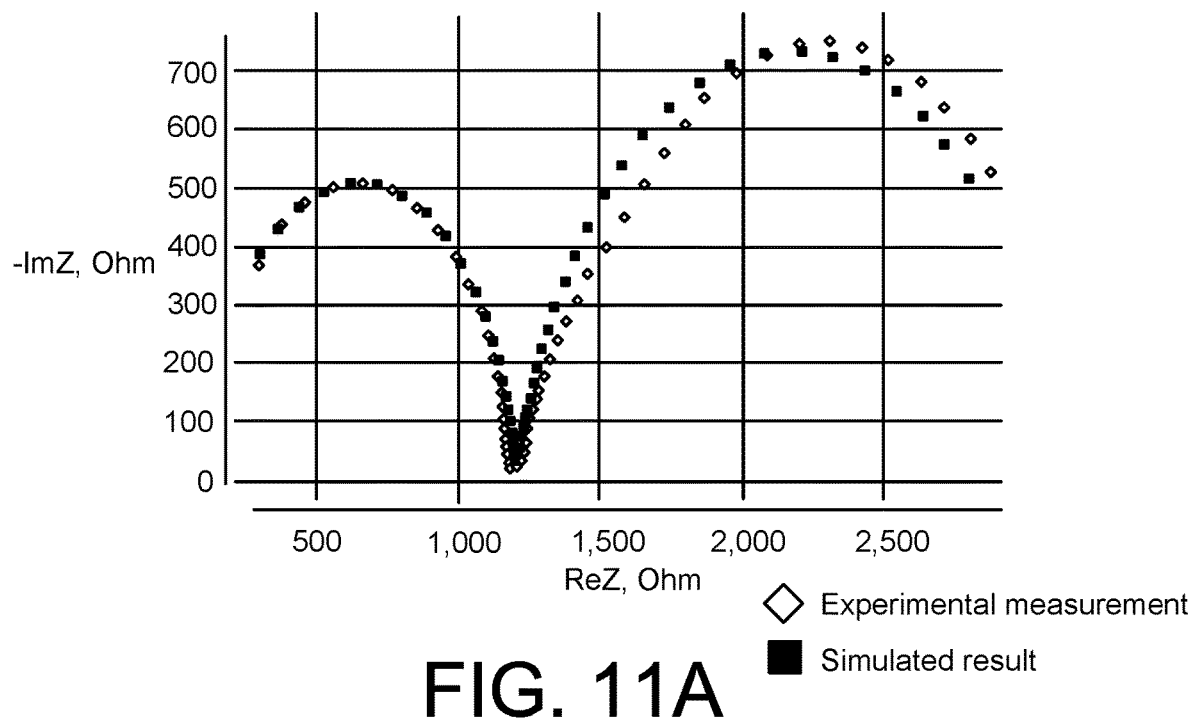
FIG. 11A is a graph of a Nyquist plot for a VANTA IDE comparing simulated results with experimental results.
Figure 11B:
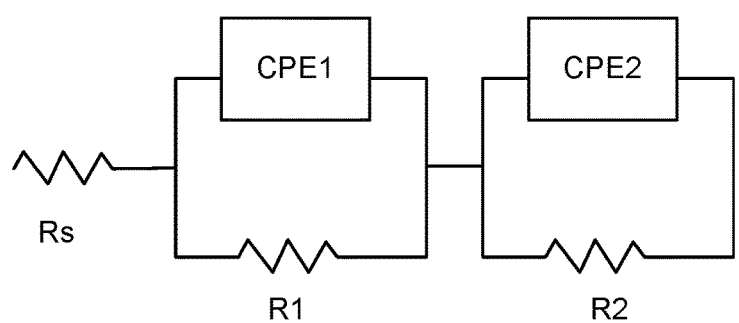
FIG. 11B is a schematic diagram illustrating an equivalent circuit used to produce the simulated results of FIG. 11A.

FIG. 11A is a graph of a Nyquist plot for a VANTA IDE comparing simulated equivalent circuit model results with experimental results. FIG. 11B is a schematic diagram illustrating an equivalent circuit used to produce the simulated results of FIG. 11A. The data in FIG. 11A illustrates the further evaluation of electrical/electrochemical behavior of VANTA IDE immunosensors, such as those described herein, using an equivalent circuit model (shown in FIG. 11B) based on IDEs operated in a faradaic EIS sensing modality (e.g., a 2-electrode potentiometric set-up without a reference electrode-the sensing modality used for immunosensing in approaches described herein).

The equivalent circuit model of FIG. 11B was created for the VANTA IDE biosensors by connecting two constant-phase-elements in parallel with a resister (CPE-R), further in series with $R_s$ (e.g., bulk solution ionic resistance according to Randles model). Since the VANTA IDEs described herein are formed from porous CNT forests, two semicircle patterns are observed in the Nyquist plot of FIG. 11A, which correspond to the two CPEs from the equivalent circuit simulation using the equivalent circuit of FIG. 11B. The parallel combination of $CPE_1$ and $R_1$ indicates the geometric capacitance of the IDE sensor and the charge transfer resistance of the film layer. The $CPE_2$ and $R_2$ components represent the capacitance and resistance at the interface between the film and the solution.

FIG. 11A illustrates a comparison of the experimental impedance (Nyquist plot) and simulated results using the circuit model for 0.1 pg/mL of concentration of Ab functionalization, clearly demonstrating close similarity. As shown in FIG. 11A, VANTA IDEs can exhibit an $R_s$ of 100Ω, $R_2$ of 2000Ω and $R_3$ of 1100Ω, while $CPE_1$ and $CPE_2$ have n values of 0.95 and 0.80 respectively, indicating $CPE_1$ acts more like a capacitor while $CPE_2$ acts more like a resistor. Fitting experimental data to the equivalent circuit, as illustrated in FIG. 11A, illustrates how each component behaves electrically in the electrolyte and changes with the increase of CIP2A concentration. In addition, it demonstrates that charge transfer resistance is largely responsible for the detection of CIP2A.

The VANTA IDEs described herein were functionalized with anti-CIP2A Ab and demonstrated a wide linear sensing range between 5 pg/mL and 400 pg/mL, in buffer (e.g., PBS), with a detection limit of 4.69 pg/mL for CIP2A Ag, a key diagnostic biomarker expressed in saliva during the early stages of oral cancer. Moreover, the evaluated VANTA IDE sensors demonstrated the capability of detecting CIP2A in saliva supernatant with a sensing range of 1-100 pg/ml, and detection limit of 0.24 pg/ml, without the need for sample pre-labeling or pre-concentration techniques. This detection limit and sensing range is much lower than the detection range (0.156 ng-10 ng/ml) reported for commercial human CIP2A ELISA kits. Further, the total sensing time for such biosensors can be less than 35 minutes (including sample incubation and signal acquisition time). Accordingly, such VANTA IDEs demonstrate a potential platform technology for oral cancer detection at the POC, and/or potential for detecting other target analyte in a saliva matrix or other biological samples.

Further, as CIP2A production is also linked to other cancers such as breast and melanoma cancers, the VANTA IDEs described herein could be modified for use in a blood or tissue matrix for multiple cancer screening applications. In fact, such VANTA IDE sensor devices may be adapted to not only function as immunosensors, but also for electrochemical biosensing in general. The 3D VANTA IDE structures described herein are conducive to Ab biofunctionalization and do not significantly interfere with immunological binding motifs, while still providing gaps in the biorecognition layer for significant charge transfer to occur during EIS measurements. Accordingly, the VANTA IDE sensors described herein enable Ag detection without the need for secondary Ab/nanoparticle labels. Furthermore, the use of faradaic EIS performed with the redox probe $[Fe(CN)_6]^{3-/4-}$ can eliminate the need for a reference electrode, or a 3-electrode electrochemical set-up. The elimination of 3-electrode patterning and a redox material makes these VANTA-IDEs well-suited for miniaturization, large scale fabrication and potential incorporation into microfluidic channels for multiplex electrochemical sensing of a wide variety of target analytes from a single sample. Moreover, the use of electrochemical devices enables POC sensing as only minimal equipment, such as a portable potentiostat (e.g., similar to a glucometer), can be used by non-technical staff to operate the screening tests. Therefore, electrochemical devices can circumvent the challenges associated with fluorescence/optical based sensors that require complex equipment/processes (e.g., fluorescence microscopes, pre-labeling steps) and that can be impeded by turbid, optically dense or autofluorescent biological samples.

Furthermore, the fabrication process for 3D CNT electrodes described herein could be applied to emerging fields that have incorporated CNTs in numerous electrochemical applications, including sensors, fuel cells, actuators, and energy harvesters.

As noted above, the approaches described herein can be useful in a number of sensing applications, and the details described for one implementation can, where appropriate, be incorporated or included in other implementations. For instance, as described above, VANTA IDE sensors can be used to accurately sense the presence of an oncoprotein (CIP2A) that is a biomarkers for various cancers, such as oral cancers. These sensors can enable point-of-care testing, such as during a routine dental exam (using a patient's saliva as a test sample). Such sensing can be performed using EIS without the need for antibody tagging or labeling, and with the need for fluorescence and/or laboratory analysis.

By using other biorecognition agents (antibodies, aptamers/DNA, enzymes, phages, peptides, etc.), rapid field testing for any number of biological analytes using such VANTA IDE sensors can also be facilitated. For example, a VANTA IDE sensor, such as those described herein, could be biofunctionalized with an antibody for detecting Methicillin-resistant *Staphylococcus aureus* bacteria (MRSA) to facilitate field testing for detecting MRSA pathogens, such as in livestock, and/or for use in human clinical settings to monitor for MRSA colonization and infection. In some implementations, other antibodies could be used for pen-side detection of cattle disease (e.g., Johne's disease), or for point-of-care screening of other cancers (e.g., prostrate, breast, and lung). Other continuous biosensors such as those used for glucose or lactate monitoring with the use of enzymes (e.g., glucose oxidase and lactate oxidase) could also be using carbon nanotube array IDEs (e.g., such as VANTA IDEs).

In a general aspect, an apparatus can include a first carbon nanotube array that is patterned to define a first electrode having a first plurality of electrode segments; and a second carbon nanotube array that is patterned to define a second electrode having a second plurality of electrode segments. The second plurality of electrode segments can be interdigitated with the first plurality of electrode segments. The apparatus can also include a biorecognition agent disposed on a surface of the first electrode and disposed on a surface of the second electrode. The first plurality of electrode segments can each having a height-to-width aspect ratio of at least 1 to 1.

Implementations can include one or more of the following features. For example, the first carbon nanotube array can be a first vertically-aligned carbon nanotube array (VANTA), and the second carbon nanotube array can be a second VANTA.

The biorecognition agent can include one of an antibody, an aptamer or an enzyme. The biorecognition agent can include an antibody specific to detection of an oncoprotein, where the oncoprotein can be a CIP2A protein and the antibody can be a PP2A cancerous inhibitor. The biorecognition agent can include an antibody specific to detection of a Methicillin-resistant *Staphylococcus aureus* (MRSA) bacteria.

The second plurality of electrode segments can each have a height-to-width aspect ratio of at least 1 to 1. The height-to-width aspect ratio of the second plurality of electrode segments can be approximately equal to the height-to-width aspect ratio of the first plurality of electrode segments. An electrode segment of the first plurality of electrode segments can have a width of approximately 25 microns (μm) and a height equal to or greater than 25 μm. A spacing between an electrode segment of the first plurality of electrode segments and an adjacent electrode segment of the second plurality of electrode segments can be in a range of 1-25 μm.

The apparatus can be configured to detect, using electrochemical impedance spectroscopy (EIS), a concentration of an analyte corresponding with the biorecognition agent.

The first carbon nanotube array and the second carbon nanotube array can be infiltrated with amorphous carbon. The first electrode and the second electrode can be hydrophobic. The first electrode and the second electrode can be hydrophilic.

In another general aspect, an apparatus can include a patterned carbon nanotube array having a height of greater than or equal to 0.5 microns (μm), amorphous carbon infiltrated in a surface of the patterned carbon nanotube array, and a biorecognition agent disposed on the surface of the carbon nanotube array.

Implementations can include one or more of the following features. For example, the biorecognition agent can include one of an antibody, an aptamer or an enzyme. The biorecognition agent can include an antibody specific to detection of an oncoprotein. The biorecognition agent can be covalently bonded with the surface of the carbon nanotube array. The biorecognition agent can include an antibody specific to detection of a Methicillin-resistant *Staphylococcus aureus* (MRSA) bacteria.

The apparatus can be configured to detect, using electrochemical impedance spectroscopy (EIS), a concentration of an analyte corresponding with the biorecognition agent.

In another genera aspect, a method can include forming a first carbon nanotube array including patterning the first carbon nanotube array to define a first electrode having a first plurality of electrode segments, and forming a second carbon nanotube array including patterning the second carbon nanotube array to define a second electrode having a second plurality of electrode segments. The second plurality of electrode segments can be interdigitated with the first plurality of electrode segments. The method can also include immobilizing a biorecognition agent on a surface of the first electrode and on a surface of the second electrode. The first plurality of electrode segments can each having a height-to-width aspect ratio of at least 1 to 1.

Implementations can include one or more of the following features. For example, the method can include, prior to immobilizing the biorecognition agent, infiltrating the surface of the first electrode and the surface of the second electrode with amorphous carbon. The method can include, prior to immobilizing the biorecognition agent, oxygen etching the first electrode and the second electrode. The method can include, prior to immobilizing the biorecognition agent, performing a bake process on the first electrode and the second electrode, the bake process being performed at a pressure that is less than atmospheric pressure.

In the foregoing disclosure, it will be understood that when an element, such as a layer, a region, or a substrate, is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element or layer, there are no intervening elements or layers present. Although the terms directly on, directly connected to, or directly coupled to may not be used throughout the detailed description, elements that are shown as being directly on, directly connected or directly coupled can be referred to as such. The claims of the application may be amended to recite exemplary relationships described in the specification or shown in the figures.

As used in this specification, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. An apparatus comprising:
    a first carbon nanotube array that is patterned to define a first electrode having a first plurality of electrode segments;
    a second carbon nanotube array that is patterned to define a second electrode having a second plurality of electrode segments, the second plurality of electrode segments being interdigitated with the first plurality of electrode segments; and
    a biorecognition agent disposed on a surface of the first electrode and disposed on a surface of the second electrode,
    the first plurality of electrode segments each having a height of greater than or equal to 1.0 micron ($\mu$m) and a height-to-width aspect ratio of at least 1 to 1.

2. The apparatus of claim 1, wherein the first carbon nanotube array is a first vertically-aligned carbon nanotube array (VANTA) and the second carbon nanotube array is a second VANTA.

3. The apparatus of claim 1, wherein the biorecognition agent includes one of an antibody, an aptamer or an enzyme.

4. The apparatus of claim 1, wherein the biorecognition agent includes an antibody specific to detection of an oncoprotein.

5. The apparatus of claim 4, wherein the oncoprotein is a CIP2A protein and the antibody is a PP2A cancerous inhibitor.

6. The apparatus of claim 1, wherein the biorecognition agent includes an antibody specific to detection of a Methicillin-resistant *Staphylococcus aureus* (MRSA) bacteria.

7. The apparatus of claim 1, wherein the second plurality of electrode segments each have a height-to-width aspect ratio of at least 1 to 1, the height-to-width aspect ratio of the second plurality of electrode segments being approximately equal to the height-to-width aspect ratio of the first plurality of electrode segments.

8. The apparatus of claim 1, wherein an electrode segment of the first plurality of electrode segments has a width of approximately 25 microns ($\mu$m) and a height equal to or greater than 25 $\mu$m.

9. The apparatus of claim 1, wherein a spacing between an electrode segment of the first plurality of electrode segments and an adjacent electrode segment of the second plurality of electrode segments is in a range of 1-25 $\mu$m.

10. The apparatus of claim 1, wherein the apparatus is configured to detect, using electrochemical impedance spectroscopy (EIS), a concentration of an analyte corresponding with the biorecognition agent.

11. The apparatus of claim 1, wherein the first carbon nanotube array and the second carbon nanotube array are infiltrated with amorphous carbon.

12. The apparatus of claim 1, wherein the first electrode and the second electrode are hydrophobic.

13. The apparatus of claim 1, wherein the first electrode and the second electrode are hydrophilic.

14. An apparatus comprising:
    a substrate;
    a patterned carbon nanotube array disposed on a surface of the substrate, the patterned carbon nanotube array having a vertical height from the surface of the substrate of greater than or equal to 0.5 microns ($\mu$m);
    amorphous carbon infiltrated in a surface of the patterned carbon nanotube array; and
    a biorecognition agent disposed on the surface of the patterned carbon nanotube array.

15. The apparatus of claim 14, wherein the biorecognition agent includes one of an antibody, an aptamer or an enzyme.

16. The apparatus of claim 14, wherein the apparatus is configured to detect, using electrochemical impedance spectroscopy (EIS), a concentration of an analyte corresponding with the biorecognition agent.

17. The apparatus of claim 14, wherein the biorecognition agent includes an antibody specific to detection of an oncoprotein, the biorecognition agent being covalently bonded with the surface of the patterned carbon nanotube array.

18. The apparatus of claim 14, wherein the biorecognition agent includes an antibody specific to detection of a Methicillin-resistant *Staphylococcus aureus* (MRSA) bacteria.

19. A method comprising:

forming a first carbon nanotube array including patterning the first carbon nanotube array to define a first electrode having a first plurality of electrode segments;

forming a second carbon nanotube array including patterning the second carbon nanotube array to define a second electrode having a second plurality of electrode segments, the second plurality of electrode segments being interdigitated with the first plurality of electrode segments; and immobilizing a biorecognition agent on a surface of the first electrode and on a surface of the second electrode, the first plurality of electrode segments each having a height of greater than or equal to 1.0 micron ($\mu$m) and a height-to-width aspect ratio of at least 1 to 1.

20. The method of claim 19, further comprising, prior to immobilizing the biorecognition agent, infiltrating the surface of the first electrode and the surface of the second electrode with amorphous carbon.

21. The method of claim 19, further comprising prior to immobilizing the biorecognition agent, oxygen etching the first electrode and the second electrode.

22. The method of claim 19, further comprising prior to immobilizing the biorecognition agent, performing a bake process on the first electrode and the second electrode, the bake process being performed at a pressure that is less than atmospheric pressure.

* * * * *